(12) United States Patent
Behfar et al.

(10) Patent No.: US 12,036,325 B2
(45) Date of Patent: Jul. 16, 2024

(54) PURIFIED EXOSOME PRODUCTS, METHOD OF MAKING, AND METHODS OF USING

(71) Applicant: MAYO FOUNDATION FOR MEDICAL EDUCATION AND RESEARCH, Rochester, MN (US)

(72) Inventors: Atta Behfar, Rochester, MN (US); Soulmaz Boroumand, Rochester, MN (US); Michael V. Callahan, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 0 days.

(21) Appl. No.: 16/771,036

(22) PCT Filed: Dec. 14, 2018

(86) PCT No.: PCT/US2018/065627
§ 371 (c)(1),
(2) Date: Jun. 9, 2020

(87) PCT Pub. No.: WO2019/118817
PCT Pub. Date: Jun. 20, 2019

(65) Prior Publication Data
US 2021/0169812 A1   Jun. 10, 2021

Related U.S. Application Data

(60) Provisional application No. 62/598,765, filed on Dec. 14, 2017.

(51) Int. Cl.
| | |
|---|---|
| *A61K 9/50* | (2006.01) |
| *A61K 9/00* | (2006.01) |
| *A61K 35/16* | (2015.01) |
| *A61K 38/39* | (2006.01) |
| *A61P 17/02* | (2006.01) |

(52) U.S. Cl.
CPC .............. *A61K 9/50* (2013.01); *A61K 9/0095* (2013.01); *A61K 9/5089* (2013.01); *A61K 35/16* (2013.01); *A61K 38/39* (2013.01); *A61P 17/02* (2018.01)

(58) Field of Classification Search
CPC ........... A61K 8/983; A61K 35/16; A61K 8/14
See application file for complete search history.

(56) References Cited

U.S. PATENT DOCUMENTS

| | | | | |
|---|---|---|---|---|
| 5,728,572 | A * | 3/1998 | Nolan ..................... | C12N 1/14 435/256.8 |
| 10,596,123 | B2 | 3/2020 | Behfar et al. | |
| 2012/0093885 | A1 | 4/2012 | Sahoo et al. | |
| 2016/0108368 | A1 | 4/2016 | Larocca et al. | |
| 2016/0324794 | A1 * | 11/2016 | Behfar ................. | A61K 9/5089 |
| 2017/0157018 | A1 * | 6/2017 | Chan ..................... | A61K 35/16 |
| 2017/0252379 | A1 | 9/2017 | Law et al. | |
| 2017/0258840 | A1 * | 9/2017 | Mitsialis ................ | A61P 35/00 |

FOREIGN PATENT DOCUMENTS

| | | |
|---|---|---|
| EP | 3 081 223 A1 | 10/2016 |
| JP | 2013-540150 A | 10/2013 |
| JP | 2017-500033 A | 1/2017 |
| WO | WO 2012/053967 A1 | 4/2012 |
| WO | WO 2015/179227 A1 | 11/2015 |
| WO | WO 2016/145330 A1 | 9/2016 |
| WO | WO 2017/023689 A1 | 2/2017 |
| WO | WO 2017/023690 A1 | 2/2017 |
| WO | WO 2017/117585 A1 | 7/2017 |
| WO | WO 2017/161010 A1 | 9/2017 |
| WO | WO 2017/163132 A2 | 9/2017 |
| WO | WO-2017173034 A1 * | 10/2017 ........... A61K 31/136 |
| WO | WO-2018070939 A1 * | 4/2018 ........... A61K 38/465 |

OTHER PUBLICATIONS

Silver et al., PSEBM 1964, 117, 656-660.*
Ahn et al., Effects of ischemia on ulcer wound healing: a new model in the rabbit ear. *Ann Plast Surg* 24, 17-23 (1990).
Chien, Ischemic rabbit ear model created by minimally invasive surgery. *Wound Repair Regen* 15, 928-935 (2007).
Chien et al., A simplified technique for producing an ischemic wound model. *J Vis Exp*, e3341 (2012).
Heath et al., Rapid isolation and enrichment of extracellular vesicle preparations using anion exchange chromatography. *Sci Rep* 8, 5730 (2018).
International Search Report and Written Opinion for PCT/US18/65627 dated May 7, 2019, 11 pages.
International Preliminary Report on Patentability for PCT/US18/65627 dated Jun. 16, 2020, 8 pages.
Kowal et al., Proteomic comparison defines novel markers to characterize heterogeneous populations of extracellular vesicle subtypes. *Proc Natl Acad Sci U S A* 113, E968-977 (2016).
Li et al., Progress in Exosome Isolation Techniques. *Theranostics* 7, 789-804 (2017).
Liang et al., In vitro scratch assay: a convenient and inexpensive method for analysis of cell migration in vitro. *Nat Protoc* 2, 329-333 (2007).
Liang et al., Role of ENPP1 on adipocyte maturation. *PLoS One* 2, e882 (2007).
Park et al., Quaternary structure of KATP channel SUR2A nucleotide binding domains resolved by synchrotron radiation X-ray scattering. *J Struct Biol* 169, 243-251 (2010).
Partial European Search Report for EP 18889223.6 dated Aug. 19, 2021, 7 pages.

(Continued)

*Primary Examiner* — Kyle A Purdy
(74) *Attorney, Agent, or Firm* — Mueting Raasch Group

(57) ABSTRACT

A purified exosome product includes spherical or spheroid exosomes with a diameter no greater than 250 nm. In some embodiments, the purified exosome product has a moisture content of no more than 10%. The purified exosome product can be reconstituted to prepare an artificial blood product.

41 Claims, 17 Drawing Sheets

(56) References Cited

OTHER PUBLICATIONS

Qi et al., Characterization of a purified exosome product and its effects on canine flexor tenocyte biology. *J Orthop Res* 38, 1845-1855 (2020).
Shi et al., A novel engineered purified exosome product patch for tendon healing: An explant in an ex vivo model. *J Orthop Res* 39, 1825-1837 (2021).
Supplementary European Search Report for EP Appl. No. 18889223 dated Nov. 19, 2021, 11 pages.
Japanese Patent Application No. 2020-532716, filed Jun. 12, 2020; Office Action issued Oct. 4, 2022, English language translation included.

* cited by examiner (A)

(B)

(C)

(D)

(A)

(B)

(C)

(D)

(A)

(B)

(A)

(B)

US 12,036,325 B2

PURIFIED EXOSOME PRODUCTS, METHOD OF MAKING, AND METHODS OF USING

CROSS-REFERENCE TO RELATED APPLICATION

This application is the § 371 U.S. National Stage of International Application No. PCT/US2018/065627, filed Dec. 14, 2018, which claims priority to U.S. Provisional Patent Application No. 62/598,765, filed Dec. 14, 2017, each of which is incorporated herein by reference in its entirety.

SUMMARY

This disclosure describes, in one aspect, a purified exosome product. In some embodiments, the purified exosome product includes spherical or spheroid exosomes with a diameter no greater than 300 nm. In some embodiments, the purified exosome product includes a population of exosomes in which at least 95% of the exosomes have a diameter that falls within a distribution range of 100 nm. In some of these embodiments, the purified exosome product includes a population of exosomes in which at least 90% of the exosomes have a diameter that falls within a distribution range of 60 nm.

In some embodiments, the purified exosome product has a moisture content of no more than 10%.

In some embodiments, the purified exosome product has a shelf life of at least six months without refrigeration.

In another aspect, this disclosure describes a reconstituted product in which any embodiment of the purified exosome product summarized above is reconstituted in water. In some embodiments, the purified exosome product is provided at a concentration of no more than 30%.

In some embodiments, the purified exosome product can include a mixture of $CD63^+$ exosomes and $CD63^-$ exosomes. In some of these embodiments, the purified exosome product can include at least 50% $CD63^-$ exosomes. In other embodiments, the purified exosome product can include from 1% to 20% $CD63^-$ exosomes and from 80% to 99% $CD63^+$ exosomes.

In another aspect, this disclosure describes a composition that generally includes a biocompatible matrix and any embodiment of the purified exosome product summarized above. In some embodiments, the biocompatible matrix can include collagen, thrombin, gelatin, alginate, or another naturally-occurring basement membrane product.

In another aspect, this disclosure describes a method of preparing a purified exosome product. Generally, the method includes obtaining starting material, filtering the starting material, pooling filtered material, agitating the pooled material, and cryodesiccating the agitated pooled material. The starting material can include blood, a blood product, or certain non-blood products. Suitable non-blood products include, for example, umbilical cord Wharton's jelly, stromal vascular fraction of fat, apheresis bone marrow products, synovial fluid, cerebrospinal fluid, or mesenchymal stem cells.

In some embodiments, the starting material is obtained from a person under the age of 30, a post-surgical donor, a pre-menopausal woman, a peripartum woman, or a placenta.

In some embodiments, the method includes, prior to cryodesiccating the agitated pooled material, freezing the agitated pooled material and thawing the frozen agitate pooled material.

In some embodiments, the material is cryodesiccated for at least five hours. In some of these embodiments, the agitated pooled material is cryodesiccated for 170 hours.

In another aspect, this disclosure describes a method for preparing an artificial blood product, the method generally includes reconstituting any embodiment of the purified exosome product summarized above in a pharmaceutically acceptable carrier.

In some embodiments, the reconstituted blood product may be prepared by mixing the purified exosome product a biodegradable polymer scaffold, a non-biodegradable polymer scaffold, or a nanotube.

In another aspect, this disclosure describes a method for accelerating wound healing. Generally, the method includes administering any embodiment of the artificial blood product summarized above to a wound in an amount effective heal the wound in less time than the wound would heal without being treated.

In another aspect, this disclosure describes a method for increasing vascularization of a wound bed. Generally, the method includes administering any embodiment of the artificial blood product summarized above to a wound in an amount effective heal the wound in less time than the wound would heal without being treated.

In another aspect, this disclosure describes a method for increasing epithelization of a wound. Generally, the method includes administering any embodiment of the artificial blood product summarized above to a wound in an amount effective heal the wound in less time than the wound would heal without being treated.

In another aspect, this disclosure describes a method for inhibiting neoplasia in a tissue. Generally, the method includes administering an embodiment of the artificial blood product containing at least 50% $CD63^-$ exosomes to a tissue exhibiting neoplasia.

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF ILLUSTRATIVE EMBODIMENTS

Figure 1:
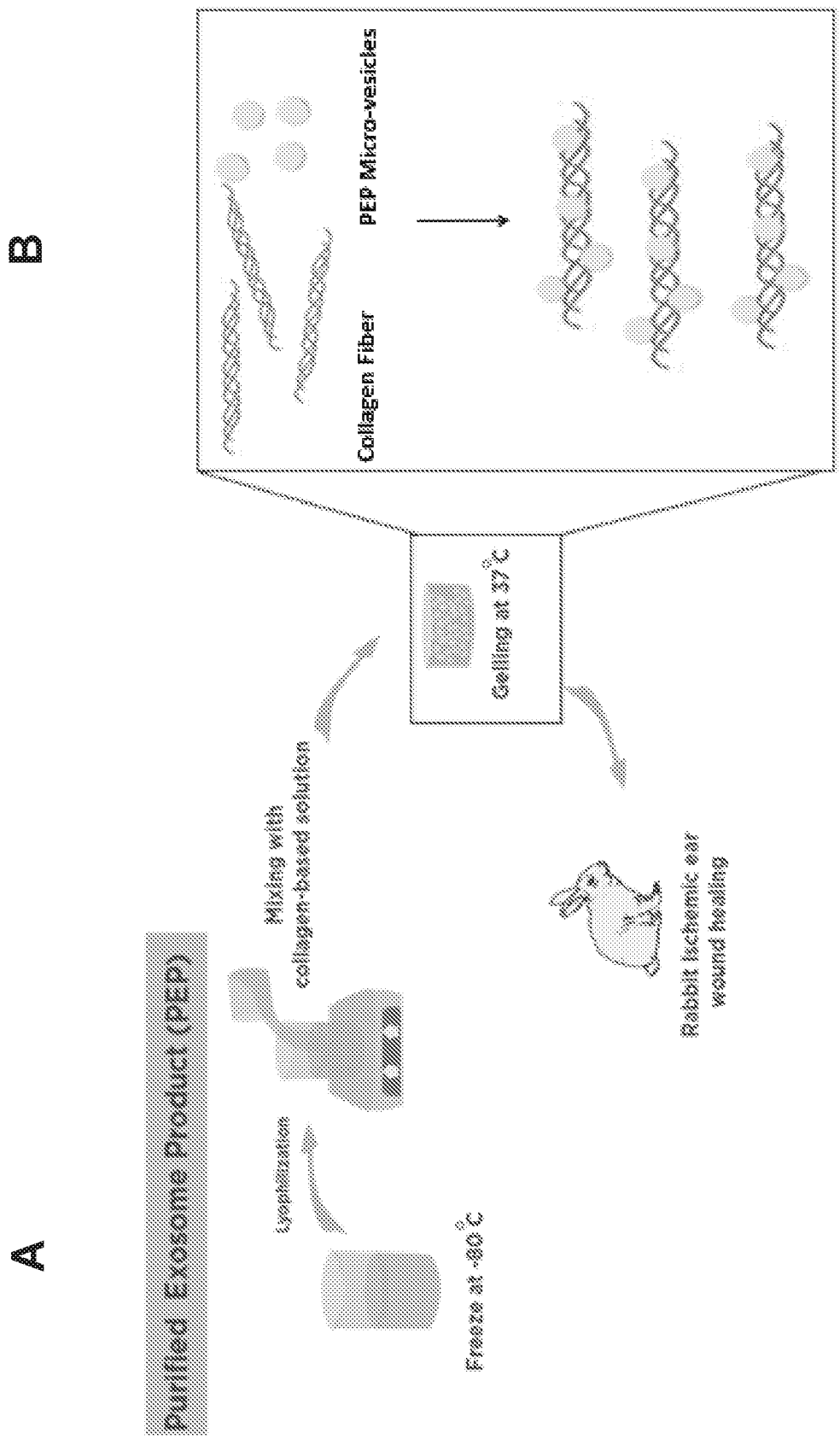
FIG. 1. Images of purified exosome product (PEP). (A) PEP and collagen bio-scaffold gel production. (B) Collagen fibers acts as carriers vessels for the PEP micro-vesicles.

This disclosure describes a novel purified exosome product (PEP) having a unique structure, compositions that include the PEP, methods of preparing the PEP, and methods of using the PEP. The method of using include various applications related to wound healing. An adequate quantity of the PEP can restore otherwise impaired wound repair.

Despite the PEP (purified exosome product) nomenclature, the products described herein can be prepared from extracellular vesicles and/or exomeres. Accordingly, unless otherwise specified in a specific context, the term "exosome" throughout this disclosure includes not only exosomes but also exomeres and extracellular vesicles so long as the product, itself, has the physical, structural, and/or functional character described for PEP.

Non-healing wounds in patients with pathophysiological defects such as diabetes, peripheral vascular disease, or infection represent a significant worldwide medical problem. The complex process of wound healing is governed by multiple biological and molecular events that occur during inflammation, proliferation, and extracellular matrix deposition.

In normal wounds, inflammatory cells, keratinocytes, fibroblasts, growth factor production, cell proliferation, and neovascularization orchestrate progression of the healing process. Inadequate growth factor production, reduced angiogenesis, and impaired cell migration are factors that interfere with normal repair processes in wounds. Indeed, impaired skin perfusion due to proximal arterial obstruction, vascular compression, or microvascular occlusion or thrombosis remains a central risk factor for non-healing wounds.

Current clinical management of non-healing wounds involves local care with debridement and proper wound dressing. Adjuncts to wound healing may include negative pressure wound therapy (NPWT) and hyperbaric oxygen therapy (HBO). Restoration of angiogenesis may reverse the disruption of the wound healing cycle and contribute to repair at a sustained, measurable rate. Also, topical application of essential wound healing growth factor by applying Platelet Rich Plasma (PRP) contributes to normal repair in various tissue repair models.

Furthermore, improvement and enhancement of diabetic wounds can be achieved using cell-derived exosomes. Effects of exosome-based therapies to accelerate wound healing and angiogenesis have been demonstrated by using body fluid-derived exosomes.

Exosomes are microvesicles (40 nm-100 nm in diameter), secreted from all different cell types and provide cell-to-cell communication signals. A variety of different cargo molecules including miRNA and proteins can be transported between cells via exosomes. Current knowledge of exosomal function in wound healing remains limited.

This disclosure describes a novel exosome composition, its preparation, and various applications for its use. In the study described herein, multiple exosome formulations were evaluated to identify the ultra-structure level. Using this approach, a novel purified exosome product (PEP) was produced having unique ultra-structure.

The starting material for preparing the PEP may be any suitable blood product including, without limitation, whole blood or any suitable apheretic blood product (including leukopheresis products, plasmapheresis product, cryo poor plasma, fresh frozen plasma, pheresis platelet products, platelet rich plasma, platelet poor plasma, or any erythrocyte depleted and leukocyte depleted product). The blood or blood product may be obtained from any suitable source, including but not limited to the general population, general population age 30 or below, general population age 40 or below, post-surgical population, a pre-menopausal woman, a peripartum woman, a placenta, or umbilical cord blood. The starting material for preparing the PEP may, alternatively, be a suitable non-blood source such as, for example, umbilical cord Wharton's jelly, stromal vascular fraction of fat, apheresis bone marrow products, synovial fluid, cerebrospinal fluid, mesenchymal stem cells, endothelial cells, neural stem cells, embryonic stem cells, induced pluripotent stem cells, or the conditioned medium of these or any other cell sources.

If necessary, the starting material may be stored frozen until needed for preparing the PEP. Typically, the starting material may be stored at −20° C. or −80° C. and, preferably, within a Current Good Manufacturing Practices (CGMP) facility.

The process for preparing the PEP begins with a filtration step. The starting material—e.g., 2-30 units (typically 5-15) of a blood product—is thawed, if necessary, prior to filtration. Gravity-based filtration is sufficient, but any suitable filtration procedure may be performed. The filtration products are pooled as a combined product with several agitation steps. Any agitation method used for adequate mixing a sample can be used. Agitation can include, for example, five minutes of manual agitation and/or mechanical agitation for 5-15 minutes, but is not limited to these options. The pooled filtration products may, if desired, be frozen to −20° C. to −80° C. and stored until ready for further processing. If stored frozen, the material may be thawed under controlled conditions—e.g., warming at a rate of from 0.1° C. to 5° C. per minute.

If desired, the filtration product may be aliquoted into, for example, glass vials. Depending on the level of moisture content desired, volumes as little as 0.1 ml to 10 ml may be used in vials as small as 1 ml and as large as 50 ml. Aliquoted products next undergo modulated temperature changes to ensure a uniform cryodesiccation profile.

Cryodesiccation can be performed at any temperatures below that at which water freezes at the atmospheric pressure (either natural or artificial) at which the cryodesiccation is being performed. Thus, in some embodiments, cryodesiccation can be performed at a minimum temperature of no colder than −180° C., no colder than −160° C., no colder than −140° C., no colder than −120° C., no colder than −100° C., no colder than −90° C., no colder than −80° C., no colder than −70° C., no colder than −60° C., no colder than −50° C., no colder than −40° C., no colder than −30° C., or no colder than −20° C. In some embodiments, cryodesiccation can be performed at a maximum temperature of no warmer than 0° C., no warmer than −5° C., no warmer than −10° C., no warmer than −15° C., no warmer than −20° C., no warmer than −25° C., no warmer than −30° C., no warmer than −35° C., no warmer than −40° C., no warmer than −45° C., no warmer than −50° C., no warmer than −55° C., no warmer than −60° C., no warmer than −65° C., no warmer than −70° C., or no warmer than −75° C. In some embodiments, cryodesiccation can be performed within a temperature range characterized by endpoints defined by any minimum temperature set forth above and any maximum temperature set forth above that is warmer than the minimum temperature. Thus, for example, in some embodiments the cryodesiccation can be performed at a temperature of from −10° C. to −100° C. In the initial freeze step, temperatures can be reduced as fast as 2 degrees per minute to as slow as 0.1 degrees per minute to achieve the desired terminal temperature.

Once the desired terminal temperature is reached, a vacuum pressure is applied for initial drying. The vacuum pressure may be any suitable vacuum pressure. Thus, in some embodiments, the minimum vacuum pressure applied may be no less than 1 mTorr, such as, for example, no less than 5 mTorr, no less than 10 mTorr, no less than 15 mTorr, no less than 20 mTorr, no less than 25 mTorr, no less than 50 mTorr, no less than 75 mTorr, no less than 100 mTorr, no less than 150 mTorr, or no less than 200 mTorr. In some embodiments, the maximum vacuum pressure applied may be no more than 500 mTorr such as, for example, no more than 400 mTorr, no more than 300 mTorr, no more than 200 mTorr, no more than 100 mTorr, no more than 90 mTorr, no more than 80 mTorr, no more than 70 mTorr, no more than 60 mTorr, or no more than 50 mTorr. In some embodiments, the vacuum pressure applied may be characterized as a range having endpoints defined by any minimum vacuum pressure set forth above and any maximum vacuum pressure set forth above that is greater than the minimum vacuum pressure. Thus, for example, the vacuum pressure applied may range from 10 mTorr to 300 mTorr.

This initial phase can be maintained for a minimum hold time of at least 15 minutes such as, for example, at least 20 minutes, at least 30 minutes, at least 40 minutes, at least 50 minutes, at least 60 minutes, at least 70 minutes, at least 80 minutes, at least 90 minutes, at least 100 minutes, at least 120 minutes, at least 140 minutes, at least 160 minutes, at least 180 minutes, at least 200 minutes, at least 220 minutes, or at least 240 minutes. The initial phase can be maintained for a maximum hold time of no more than 30 days such as, for example, no more than 15 days, no more than 10 days, no more than 5 days, no more than 1 day, no more than 1200 minutes, no more than 900 minutes, no more than 600 minutes, no more than 300 minutes, no more than 270 minutes, no more than 240 minutes, no more than 210 minutes, no more than 180 minutes, no more than 150 minutes, no more than 120 minutes, no more than 90 minutes, no more than 75 minutes, no more than 60 minutes, or no more than 45 minutes. In some embodiments, the initial phase can be maintained for a hold time characterized as a range having endpoints defined by any minimum period set forth above and any maximum period set forth above that is great than the minimum period. In certain embodiments, for example, the initial phase can be maintained for a hold time of from 30 minutes to 300 minutes.

Depending on the starting volume, additional drying steps and alterations in terminal temperatures may be desired. For any additional drying step, the terminal temperature can be any temperatures below that at which water freezes at the atmospheric pressure (either natural or artificial) at which the cryodesiccation is being performed. Suitable terminal temperatures are the same as set forth above for the initial drying step. When more than one drying step is included in the cryodesiccation process, the terminal temperature of each drying step may be determined independently of the terminal temperature of the initial drying step and/or independent of any additional drying step. In some embodiments, an additional drying step may be performed at a temperature of from −10° C. to −100° C. In other embodiments, an additional drying step may be performed at a temperature of from −20° C. to −140° C.

When more than one drying step is included in the cryodesiccation process, the vacuum pressure of each drying step may be determined independently of the vacuum pressure of the initial drying step and/or independent of any additional drying step. In some embodiments, the vacuum pressure for an additional drying step can range from 10 mTorr to 300 mTorr. In other embodiments, the vacuum pressure for an additional drying step can range from 50 mTorr to 400 mTorr.

When more than one drying step is included in the cryodesiccation process, the hold time of each drying step may be determined independently of the hold time of the initial drying step and/or independent of any additional drying step. In some embodiments, the hold time for an additional drying step can range from 30 minutes to 300 minutes. In other embodiments, the hold time used in an additional drying step can range from 200 minutes to 7,200 minutes.

In some embodiments, a drying step at warmer temperatures may be additionally desired. This drying step at warmer temperatures may be performed at a temperature ranging from 0° C. to 42° C. under a vacuum. The vacuum pressure may be as described immediately above for any additional drying step. The drying step at warmer temperature may be performed for any time suitable to achieve a moisture level of 10% or lower. In some embodiments, achieving such a moisture level may take from 30 minutes to 7,200 minutes, depending upon the temperature and vacuum pressure conditions.

Thus, optimal cryodesiccation parameters are based, at least in part, on the capacity of the device utilized, moisture content of starting material, starting volume, and density of starting material (e.g., serological material versus culture medium).

To achieve a lyophilized product, a caking agent may be used for specific applications, but are not necessary to derive PEP. Suitable caking agents include, but are not limited to, polyvinylpyrrolidone (PVP), dextrose, glycine, and amorphous sugars (e.g., sucrose, trehalose, mannitol). In certain embodiments, the cryodesiccation process can take as little as five hours and as long as 170 hours. The final product after this procedure is visually released based on caked pellet formation, with release criteria requiring more than 95% appropriate caking per lot manufactured. If these metrics are not met, the entire lot is decommissioned.

The PEP possesses a structure that is different than the structure of convention exosomes prepared using conventional techniques. Conventionally concentrated exosomes exhibit a structure that resembles a snowflake (irrespective of lyophilization status), as shown in FIG. 3A and FIG. 3B. In contrast, exosomes of the PEP described herein are smaller and more spherical, as shown in FIG. 3C and FIG. 3D. On atomic force microscopy and SEM, derived PEP product was found to be significantly spherical and devoid of exosome clumping versus "snow-flake" like aggregated exosome structures that are seen with processes that involve any sheering force, filtration, or centrifugation.

Thus, in some cases, the PEP is distinguishable from conventional exosome products by being spherical or spheroidal rather than crystalline in structure, having a diameter of no more than 300 nm. A PEP exosome may therefore have a maximum diameter that is no more than 300 nm such as, for example, no more than 250 nm, no more than 200 nm, no more than 175 nm, no more than 150 nm, no more than 125 nm, no more than 100 nm, no more than 95 nm, no more than 90 nm, no more than 85 nm, no more than 80 nm, no more than 75 nm. A PEP exosome may have a minimum diameter of at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, or at least 80 nm. In some cases, the diameter of the PEP exosomes may be expressed as a range having endpoints defined by any minimum diameter set forth above and any maximum diameter set forth above that is greater than the minimum diameter. In some embodiments, therefore, the PEP may be characterized as having a diameter of from 50 nm to 200 nm, such as, for example, from 100 nm to 200 nm.

Figure 14:
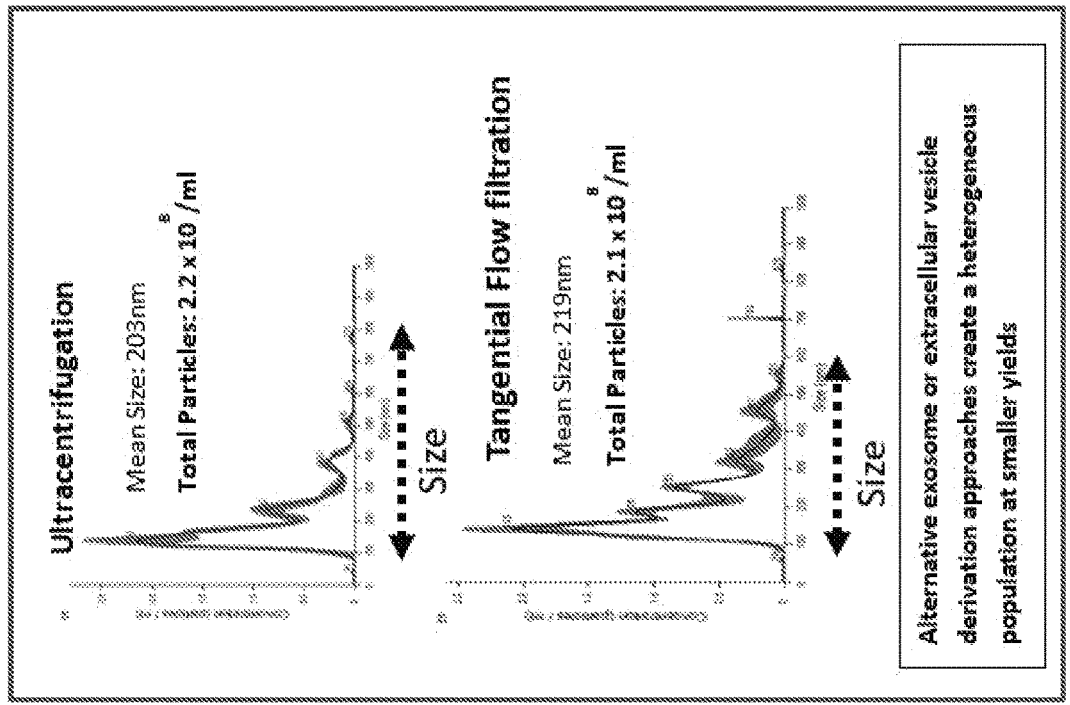
FIG. 14. Analysis of PEP versus extracellular vesicles (EV) or exosomes derived with alternative conventional methods. Ultracentrifugation and Tangential flow filtration are two established methods to concentrate exosomes or EVs out of solution. Here, NanoSight-based analysis of exosome size and quantity reveals a highly heterogeneous population of EVs when these methodologies are employed with size ranges>200 nm and particle counts well below $1\times10^{10}$/ml. Alternatively, the PEP methodology of derivation achieves a very narrow range in size of exosomes (<100 nm) and provides a particle yield greater than $1\times10^{10}$.

Moreover, FIG. 14, as explained in more detail below, provides data showing that the PEP preparations described herein can have a narrower distribution of diameters compared to conventional exosome preparations. For example, in some embodiments, the diameters of exosomes in a PEP preparation can have a distribution—i.e., the difference between the largest diameter and the smaller diameter—of less than 300 nm. FIG. 14 shows conventional exosome preparations having a distributions of diameters of 600 nm or more. FIG. 14 shows a PEP preparation where more than 95% of the exosomes have a diameter that falls within a 100-nm distribution between 100 nm in diameter and 200 nm in diameter and 90% of the exosomes have a diameter that falls within a 60-nm distribution (132 nm+/−30 nm).

In some embodiments, the PEP may possess a low moisture content, such as, for example, a moisture content of no more than 10%, no more than 9%, no more than 8%, no more than 7%, no more than 6%, no more than 5%, no more than 4%, no more than 3%, no more than 2%, or no more than 1%.

Figure 2:
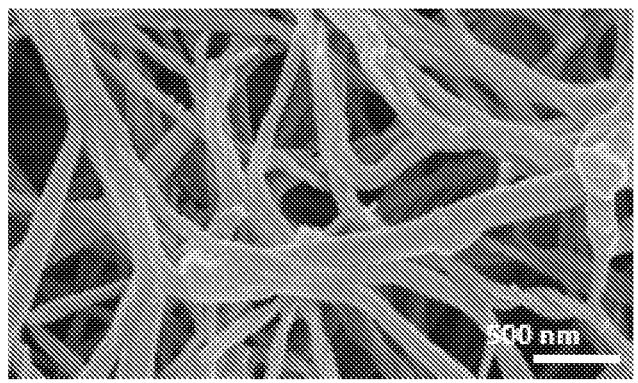
FIG. 2. Field Emission-Scanning Electron Microscopy (Fe-SEM) of the collagen scaffold with different concentrations of the purified exosomal product (PEP). (A) Collagen only; (B) Collagen with 5% PEP: (C) Collagen with 10% PEP; (D) Collagen with 20% PEP.
Figure 2:
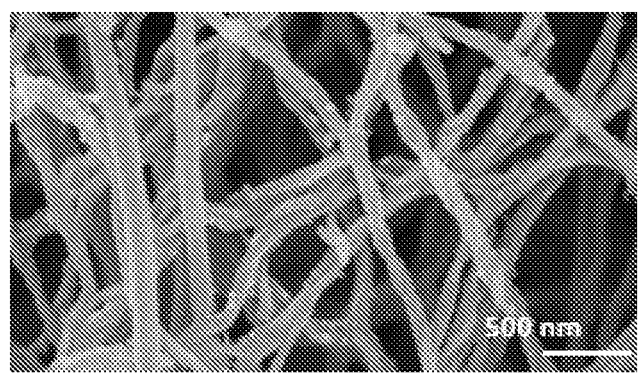
Figure 2:
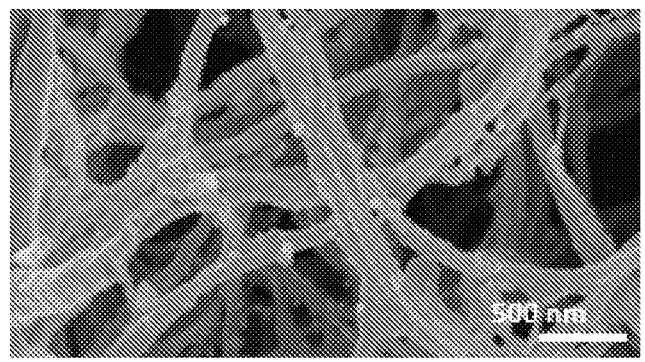
Figure 2:
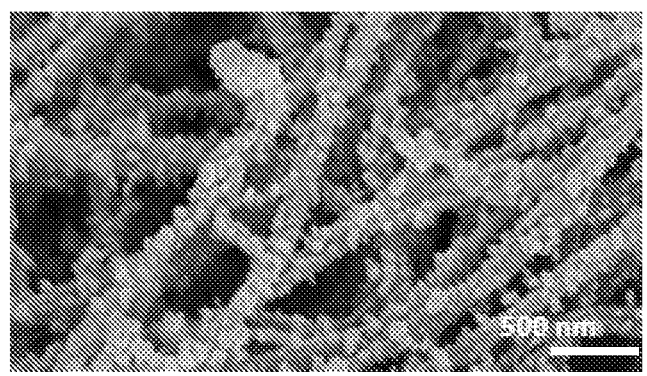
Figure 3:
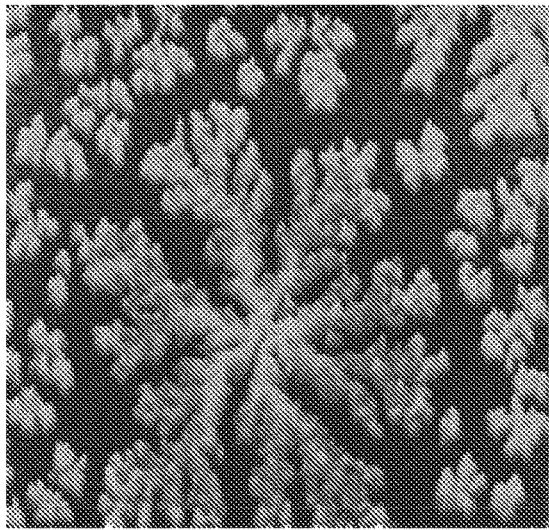
FIG. 3. Atomic Force Microscopy Imaging showing platelet rich plasma (PRP) under different magnifications (A, B) and purified exosomes (PEP) under different magnifications (C, D).
Figure 3:
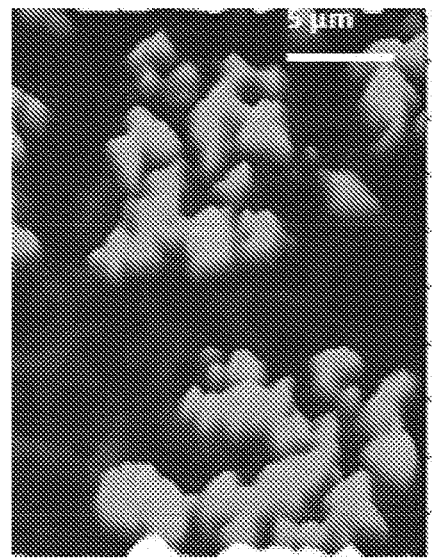
Figure 3:
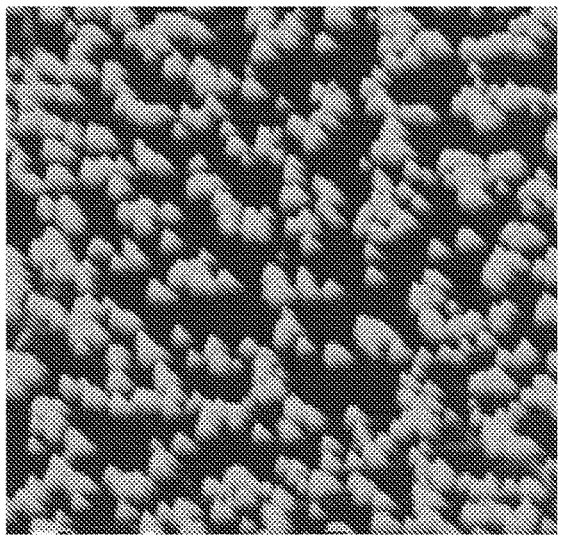
Figure 3:
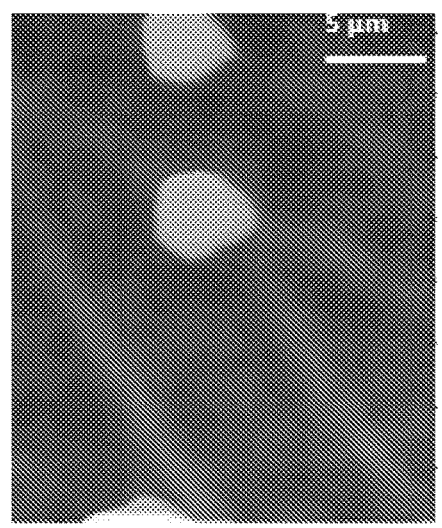

The PEP may be formulated and/or reconstituted with a pharmaceutically acceptable carrier to form a therapeutic composition. As used herein, "carrier" includes any solvent, dispersion medium, vehicle, diluent, isotonic agent, physiological buffer, carrier solution, suspension, colloid, water, and the like. The use of such media and/or agents for pharmaceutical active substances is well known in the art. Except insofar as any conventional media or agent is incompatible with the active ingredient, its use in the therapeutic compositions is contemplated. Supplementary active ingredients also can be incorporated into the compositions. As used herein, "pharmaceutically acceptable" refers to a material that is not biologically or otherwise undesirable, i.e., the material may be administered to an individual along with PEP without causing any undesirable biological effects or interacting in a deleterious manner with any of the other components of the therapeutic composition in which it is contained. Exemplary pharmaceutically acceptable carriers include, for example, a physiological buffer, distilled water, biodegradable polymer, artificial polymer, or a basement membrane solution of any suitable concentration. Additional suitable carries for PEP include any substance that has the capacity under temperature, pressure, or other environmental change to change states from liquid to solid. In this situation, PEP would be dissolved in such a substance in the liquid phase and would be incorporated (trapped) into the material once solid as illustrated in FIG. 2 and FIG. 3 in the context of an exemplary embodiment where the carrier is collagen The PEP may therefore be formulated into a therapeutic composition. The therapeutic composition may be formulated in a variety of forms adapted to a preferred route of administration. Thus, a therapeutic composition can be administered via known routes including, for example, oral, parenteral (e.g., intradermal, transcutaneous, subcutaneous, intramuscular, intraarterial, intracoronary, intravenous, intraperitoneal, etc.), or topical (e.g., intranasal, intrapulmonary, intramammary, intravaginal, intrauterine, intradermal, transcutaneous, rectally, etc.). A therapeutic composition can be administered to a mucosal surface, such as by administration to, for example, the nasal or respiratory mucosa (e.g., by spray or aerosol). A composition also can be administered via a sustained or delayed release. In addition, PEP either in solution form or in combination with above described matrices/gels may be surgically implanted within different organs or body cavities. For reconstructive, dental, or cosmetics applications, PEP may be delivered in liquid form or in combination with a matrix to, for example, subcutaneous, submucosal, or deep fascial planes.

Thus, the PEP may be provided in any suitable form including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including such as, for example, an adjuvant, a skin penetration enhancer, a thickener, and the like. Additionally, the use of PEP may be applied in combination with abrasive procedures such as microdermabrasion, microneedle, laser peel, chemical peel, or other derm-abrasive platforms. In these settings, PEP would be delivered either in solution, in a base, or as a matrix/gel. Furthermore, in hair restoration, PEP may be delivered as described above or via subcutaneous delivery.

A formulation may be conveniently presented in unit dosage form and may be prepared by methods well known in the art of pharmacy. Methods of preparing a composition with a pharmaceutically acceptable carrier include the step of bringing the PEP into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

PEP may be combined with other excipients that may modulate the structural behavior of the reconstituted/rehydrated exosome product. Suitable excipients include, for example, a biological matrix that includes collagen, thrombin, gelatin, alginate, or any other naturally occurring basement membrane product applied either as a mixture or in purified form (including decellularized tissue scaffolds). Suitable excipients also include, for example, hyaluronic acid or thrombin glue to promote rapid aggregation for filling surgical or fistulizing defects. PEP is compatible with any additive or excipient that has the capacity under temperature, pressure or other environmental change to change states from liquid to solid.

As noted above, PEP may be provided in a low moisture formulation. In some embodiments, therefore, a PEP formulation may have a shelf-life of at least six months but as long as four years without refrigeration. Thus, the PEP formulations may be particularly suitable for use in areas where wound healing is required but refrigeration is impossible, inconvenient, or costly such as, for example, underdeveloped locations or for military use. Low-moisture PEP formulations are readily resolubilized to form a reconstituted PEP product. For example, a dried PEP formulation may be resolubilized as a solution of up to 20% in less than five minutes. A 20% solution of reconstituted PEP can form a gel over a period of an hour at 37° C. A gel formulation can, for example, promote localization of the PEP after being administered to a subject and/or create structural elements that promote regenerative effects of the PEP on the tissue in need of repair. Combining the PEP with collagen can increase the rate at which the reconstituted PEP forms a gel at 37° C. Indeed, the rate at which the reconstituted PEP gels in the presence of collagen is influenced, at least in part, by the concentration of collagen. Increasing rates of gelation can be achieved using higher concentrations of collagen, with a maximum concentration of 10 mg/ml. In some embodiments, PEP is used in combination with collagen at a collagen concentration of about 5 mg/ml. Combination with other gelling materials including thrombin glue (e.g., TISSEEL, Baxter Healthcare Corp., Deerfield, IL), hyaluronic acid, polyvinyl alcohol (PVA), poly(lactic-co-glycolic acid) (PLGA), and others. When PEP is formulated as a gel with collagen, the PEP exosomes can attach to collagen fibrils, creating a "beads on a string" appearance. In addition to this, other SEM characteristics are seen with PEP depending on the osmolarity of the dissolving solution including exosomes stacked on a string, spikes on a string, or a blossoming pattern on a string. This effect is more common using PEP solutions having a concentration of, for example, from about 5% to about 30% depending, at least in part, on the type of collagen and concentration of purified collagen solution.

Whether associated with collagen or in solution, the PEP exosomes exhibit no evidence of secondary aggregation of more than 10%-20% of PEP exosomes. Moreover, there is no evidence of aggregates that include more than three exosomes. As mentioned above, the only exception to this is when PEP is rehydrated in solutions of high osmolar concentration such as the $CaCl_2$ solution for TISSEEL.

The amount of PEP administered can vary depending on various factors including, but not limited to, the weight, physical condition, and/or age of the subject, and/or the route of administration. Thus, the absolute amount of PEP included in a given unit dosage form can vary widely, and depends upon factors such as the species, age, weight and physical condition of the subject, and/or the method of administration. Accordingly, it is not practical to set forth generally the amount that constitutes an amount of PEP effective for all possible applications. Those of ordinary skill in the art, however, can readily determine the appropriate amount with due consideration of such factors.

In some embodiments, the method can include administering PEP exosomes to a subject, such as, for example, in a solution having a PEP concentration of at least 0.5% and no more than 100%. PEP exosomes may be administered to a subject at a minimum concentration of at least 1% such as, for example, at least 2%, at least 3%, at least 4%, at least 5%, at least 6%, at least 7%, at least 8%, at least 9%, at least 10%, at least 15%, at least 20%, at least 25%, at least 30%, at least 40%, or at least 50%. PEP exosomes may be administered to a subject at a maximum concentration of no more than 100% such as, for example, no more than 75%, no more than 50%, no more than 25%, no more than 20%, no more than 19%, no more than 18%, no more than 17%, no more than 16%, no more than 15%, no more than 14%, no more than 13%, no more than 12%, no more than 11%, no more than 10%, no more than 9%, no more than 8%, no more than 7%, no more than 6%, no more than 5%, no more than 4%, no more than 3%, or no more than 2%. In some embodiments, PEP exosomes may be administered to a subject in a dose within a range having endpoints defined by any minimum concentration set forth above and any maximum concentration set forth above that is greater than the minimum concentration. Thus, for example, PEP exosomes may be delivered to a subject at a concentration of at least 1% to no more than 30%, such as, for example, at least 5% to no more than 20%.

In some embodiments, the PEP may be administered, for example, from a single dose to multiple doses per week, although in some embodiments the method can be performed by administering the PEP at a frequency outside this range. The broad range of applications for which administering a PEP composition is useful makes it impractical to identify the dosing regimen for each application. In certain embodiments, the PEP may be administered from about once per month to about five times per week. For example, a single administration may be sufficient for treating, for example, myocardial infarction. For other applications—e.g., wound healing, cosmetic applications, hair regeneration-weekly or daily administration may be preferred.

The PEP compositions and formulations described herein have many applications. PEP can, for example, augment growth of mesenchymal stems cells (MSCs) and/or dermal fibroblasts to a degree greater than conventional treatments (e.g., platelet lysate) or fetal bovine serum. Similarly, PEP can induce bone differentiation, cartilage differentiation, and/or fat differentiation to a degree greater than conventional treatments (e.g., platelet lysate) or fetal bovine serum. PEP also can maintain growth of myoblasts to a degree greater than conventional treatments (e.g., platelet lysate) or fetal bovine serum. PEP may be employed to enhance growth profiles in cells used for immunotherapies such as, but not limited to, CAR-T, TRuC-T, NK-CAR, and hematopoietic stem cells.

For example, PEP compositions and formulation can induce a broad array of cellular responses that are primarily focused around proliferation, anti-apoptosis, immune regulation, and new blood vessel formation. Injured tissues in the presence of PEP have a propensity towards regeneration. This response is embodied with observations that document augmented expression of transforming growth factor beta (TGF-β, e.g., 50 pg/ml to 200 ng/ml depending on PEP exosome concentration in solution), vascular endothelial growth factor (VEGF, e.g., 10 pg/ml to 2 ng/ml depending on PEP exosome concentration in solution), epidermal growth factor (EFG, e.g., 500 pg/ml to 50 ng/ml depending on exosome concentration in solution), fibroblast growth factor (FGF, e.g., 5 pg/ml to 1 ng/ml depending on PEP exosome concentration in solution), HGF (50 pg/ml to 200 ng/ml depending on exosome concentration in solution), and PDGF (all subtypes including AA, BB, AB spanning concentrations between 5 pg/ml and 300 ng/ml depending on exosome concentration in solution). The response is not limited to these factors but the observation that these factors are induced in different tissues is an embodiment of the regenerative influence of PEP.

PEP Treatment Increases Wound Confluence Following In Vitro Scratch Assay

Figure 4:
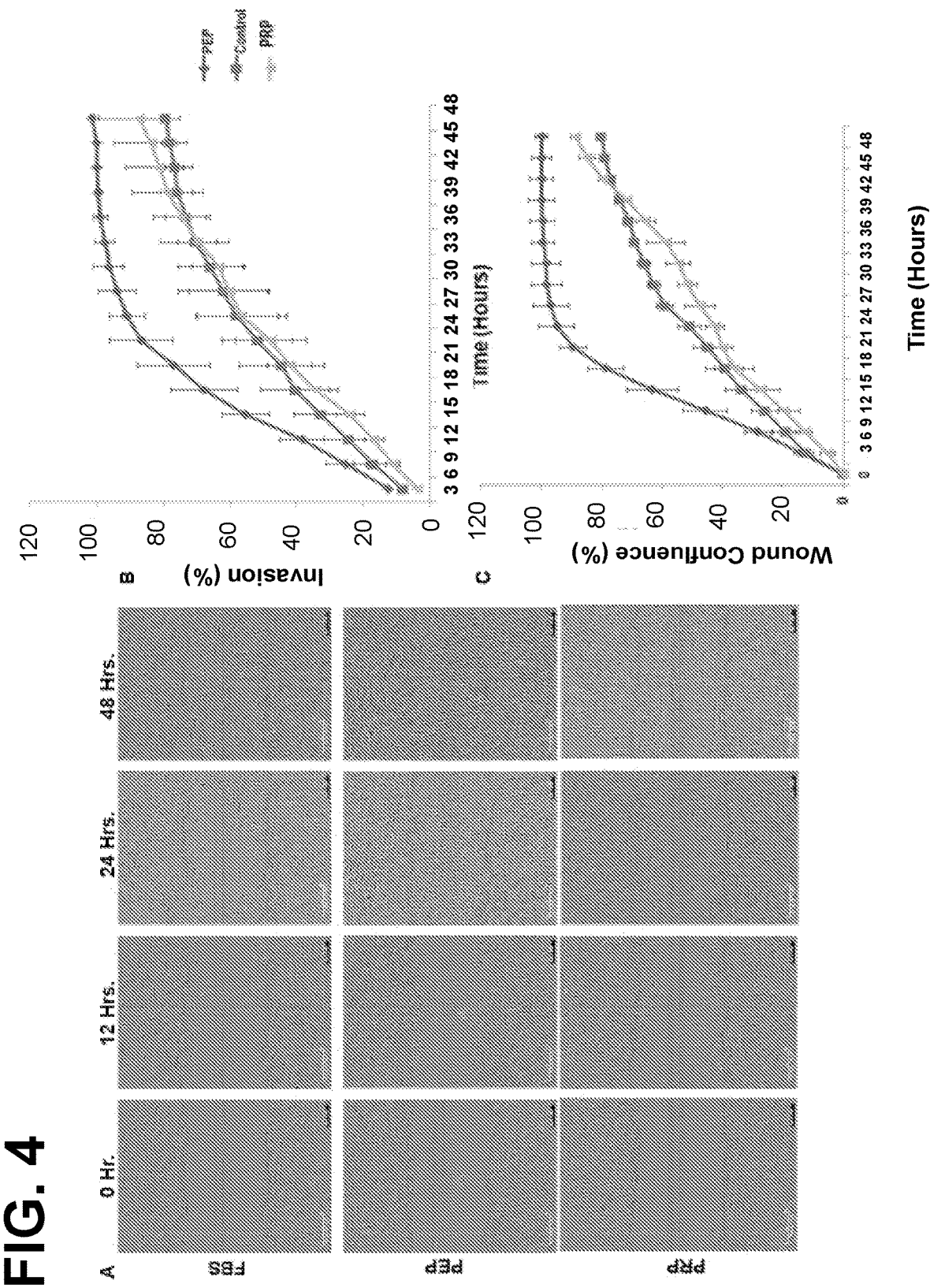
FIG. 4. In vitro cell migration scratch assay. (A) Human Dermal Fibroblast (HDF) analysis of PEP-treated, PRP-treated, and untreated (FBS) at 0 hours, 12 hours, 24 hours, and 48 hours indicates an increased rate of migration with PEP treatment; pink margins delineate the scratch area. (B) Line graph presentation of the data imaged in (A). (C) Quantification of wound confluence percentage by IncuCyte Essen BioScience is shown, demonstrating greater cell growth ratio with bio-scaffold-treated HDF.

The effect of PEP on human dermal fibroblast (HDF) migration was compared and platelet-rich plasma (PRP) treatment using the in vitro scratch assay, previously described as the gold standard to study cell migration (Liang et al., 2007. Nat Protoc 2:329-333). Treatment with PEP produced an increased rate of HDF migration compared to control and PRP-treated fibroblasts (FIG. 4). In accordance, quantitative measurement of scratch assay demonstrated higher percentage of both wound invasion (FIG. 4B) and wound confluence (FIG. 4C) in PEP-treated HDF conditions compared to control and PRP-treated HDF at 48 hours. Following the scratch assay, wound confluence of PEP treated HDF was 98% at 24 hours and over 100% at 48 hours compared to control HDF, which was 57% at 24 hours and 81% at 48 hours.

PEP Treatment Increases Tube Length

Figure 5:
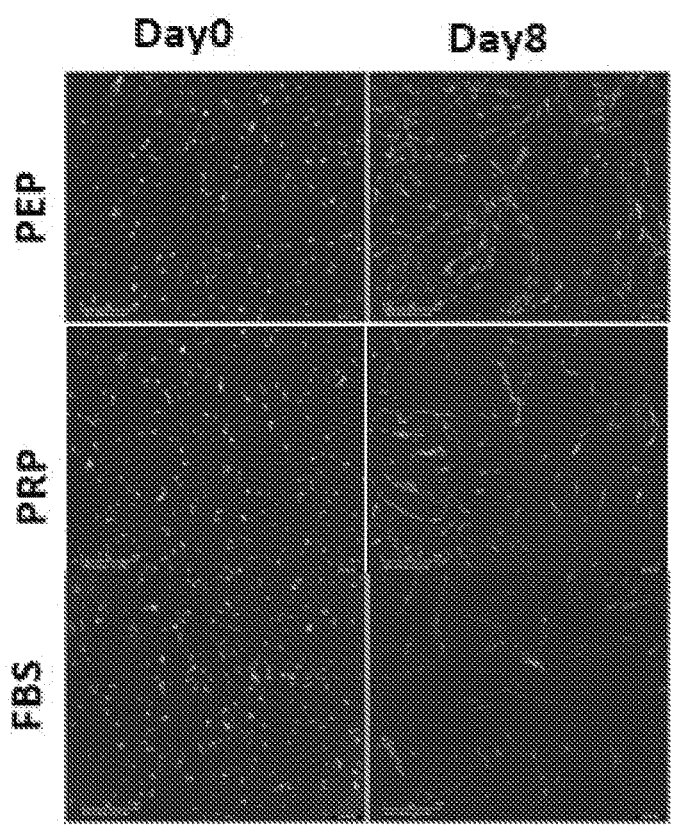
FIG. 5. PEP stimulation of angiogenesis in vitro. (A) Co-cultures of NHDF and HUVEC cells were seeded on Day 0 and Day 8 in PEP, PRP, or FBS. (B) Representative masked images of stimulated angiogenic networks after 8 days. Data are representative of two separate experiments presented as the mean±SEM (n=8). Scale Bar is 800 μm.
Figure 5:
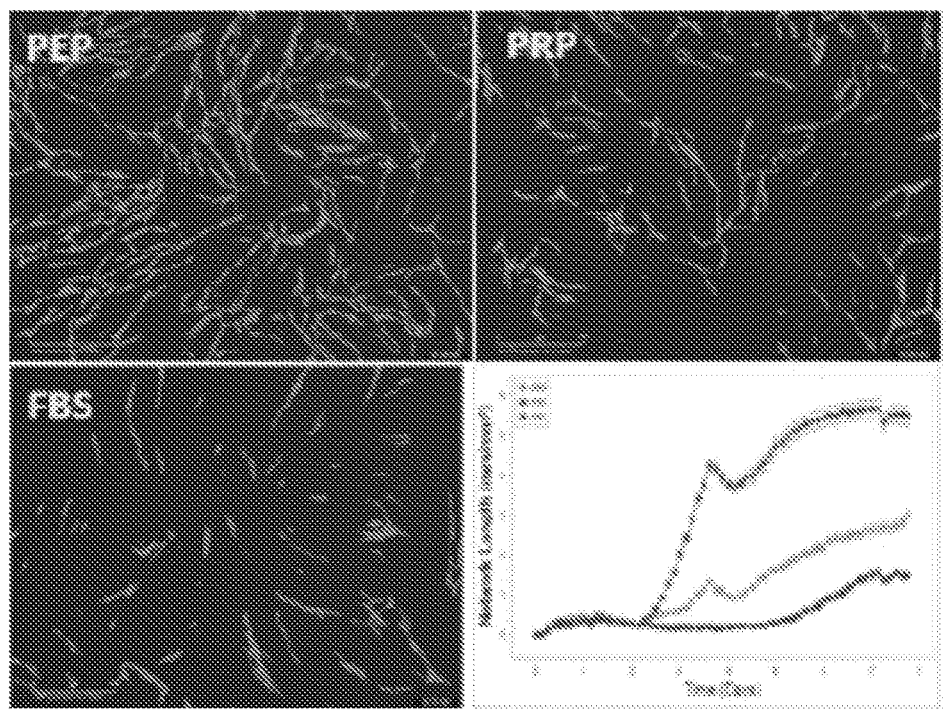

The basement membrane matrix tube formation assay can be used to study the signaling pathways of angiogenesis. In fact, PEP-treated Human Umbilical Vein Endothelial Cells (HUVEC) showed rapid basal level of tube formation, suggesting optimal conditions for wound bed angiogenesis (FIG. 5). Quantification of total network length yielded>15,000 microns (p-value p<0.001) in PEP growth conditions compared to 5000 microns in control (FIG. 5B). Interestingly, PRP treatment also moderately increased tube formation 10,000 microns (p-value<0.001) Taken together, these results indicate that PEP treatment increases in vitro rate of migration, proliferation, and tube formation correlating with known standards of in vivo re-epithelialization and vascular density.

Postoperative Appearance of Ischemic Wounds and Wound-Healing Times

A minimally-invasive rabbit ear model of ischemic wound healing (Chien, S. & Wilhelmi, B. J., 2012. *J Vis Exp*, e3341; Chien, S., 2007. *Wound Repair Regen* 15:928-935) was used to validate vessel ligation. Ischemic wounds were treated with either PEP or collagen only for four weeks (one treatment/week) and the degree of wound healing was compared to non-ischemic wounds and untreated ischemic wounds (FIG. 6A). Quantification of wound size demonstrated that PEP-treated wounds had faster closure compared to collagen-treated and untreated ischemic wounds (FIG. 6A, 6B). Specifically, 2-cm PEP-treated wounds reduced to 0.05 mm at Day 28 compared to collagen-treated wounds, which reduced to 0.67 mm at Day 28; non-ischemic wounds reduced to 0.06 mm at Day 28 and untreated ischemic wounds reduced to 1.3 mm at Day 28 (FIG. 6A, 6B). Treatment with either collagen or PEP resulted in enhanced epithelialization, at Week 4. This was corroborated by kertain-14 staining (FIG. 7A, 7B). Thus, PEP treatment accelerates wound closure and endothelial cell migration in an in vivo ischemic model.

Morphometry Evaluation for Endothelial Marker, vWF

Figure 6:
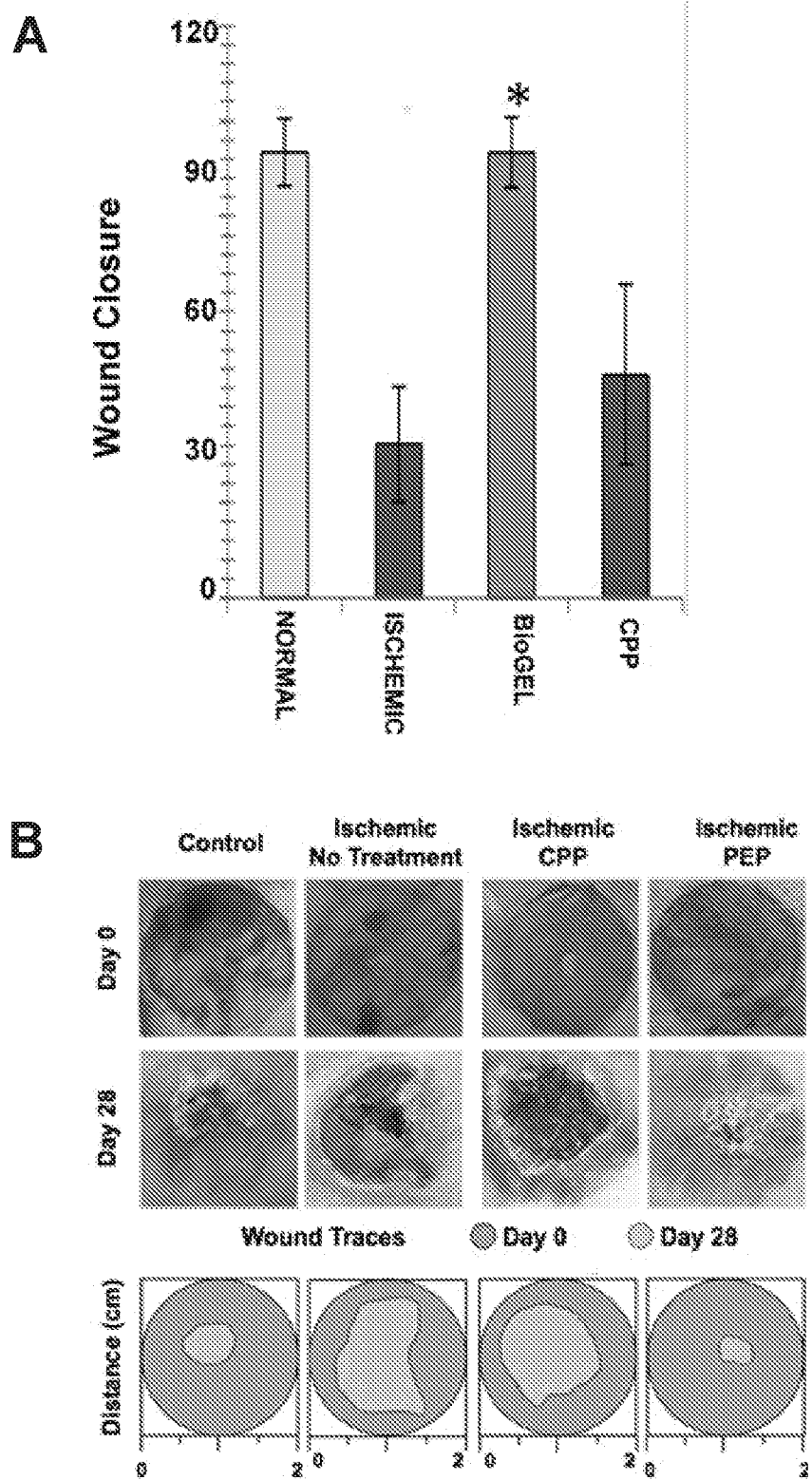
FIG. 6. Effects of PEP on wound closure. (A) Quantification of wound size demonstrated that bio-gel treated wounds had faster closure compared to collagen-treated and untreated wounds. These data are shown as average+s.t.d. Statistical significance performed using student-t test. (*=p<0.0001 and =p<0.01). (B) Top: Representative images of wound closure at Day 0 and Day 28 of 28-day in vivo rabbit ischemic ear experiments. Bottom: Traces of wound bed closure during 28 days in vivo for each treatment group.
Figure 7:
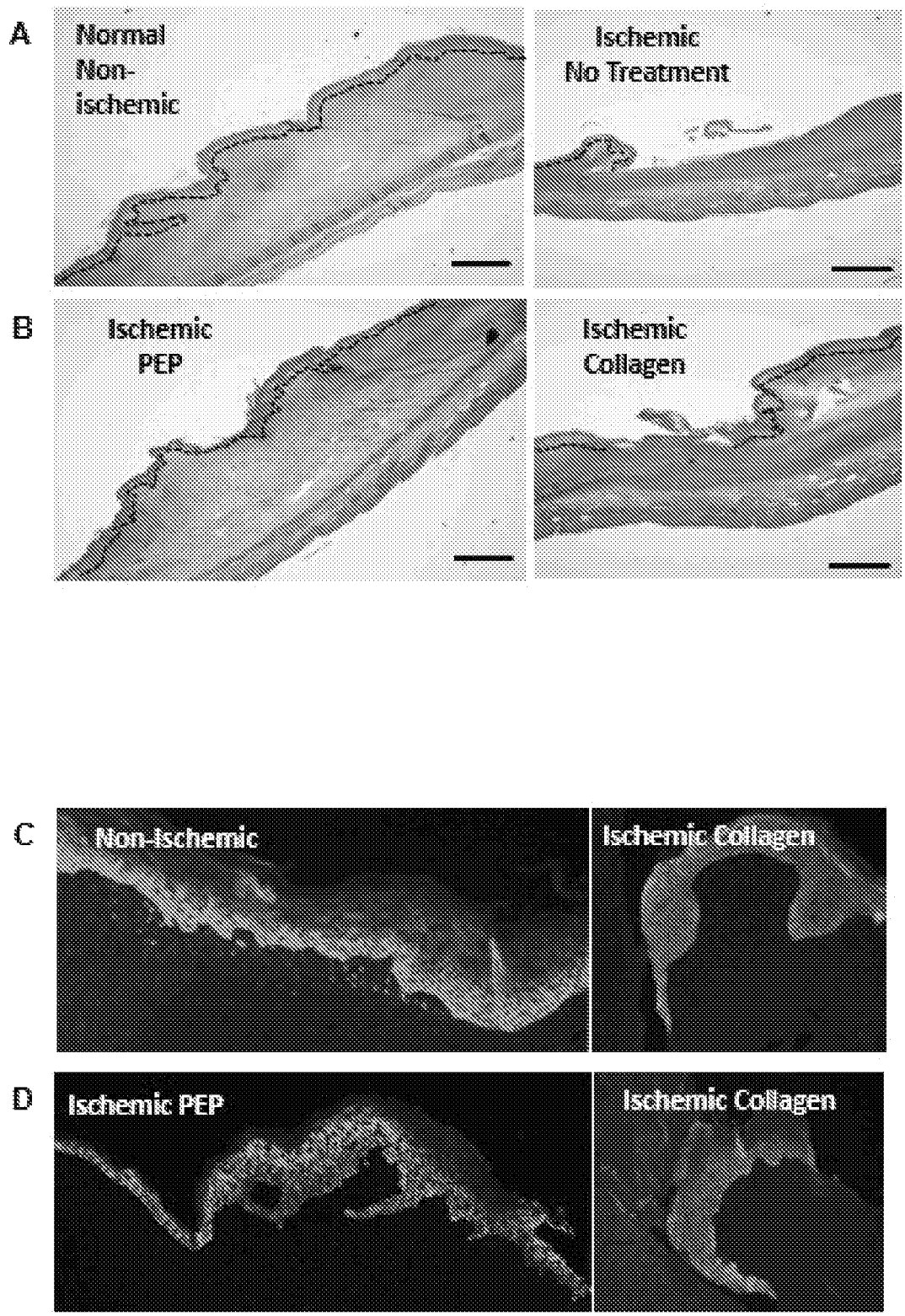
FIG. 7. Histological analysis of ischemic wound healing at postoperative week 2. (A and B) Representative H&E images are shown for each treatment: non-ischemic control, ischemic untreated control, ischemic wound plus collagen, and ischemic wound plus PEP. Scale bar: 1 mm; 20×. (C and D) Rabbit ears ischemic wounds demonstrate marked cellular infiltration and increased epidermal thickness at the wound edge. H&E, Hematoxylin and eosin.

Wound samples stained with sheep polyclonal vWF antibody show higher vWF stained cells in the wounds treated with bio-gel (including the PEP-collagen scaffolds shown in FIG. 2) when compared with untreated control and collagen-treated wounds or reconstituted PEP as a 10-20% solution rehydrating a dry collagen scaffold—see FIGS. 6 and 7 with PEP enriched collagen scaffolds improving wound healing towards a state seen with non-ischemic wounds). A quantitative analysis confirmed that there was a statistically significant difference (p<0.01) between the bio-gel treated group (53.7% endothelial cells/field; n=3) and the untreated group (22.2% endothelial cells/field; n=3), corresponding with greater angiogenesis.

∝-SMA Expression in Wound Site Treated by PEP

Figure 8:
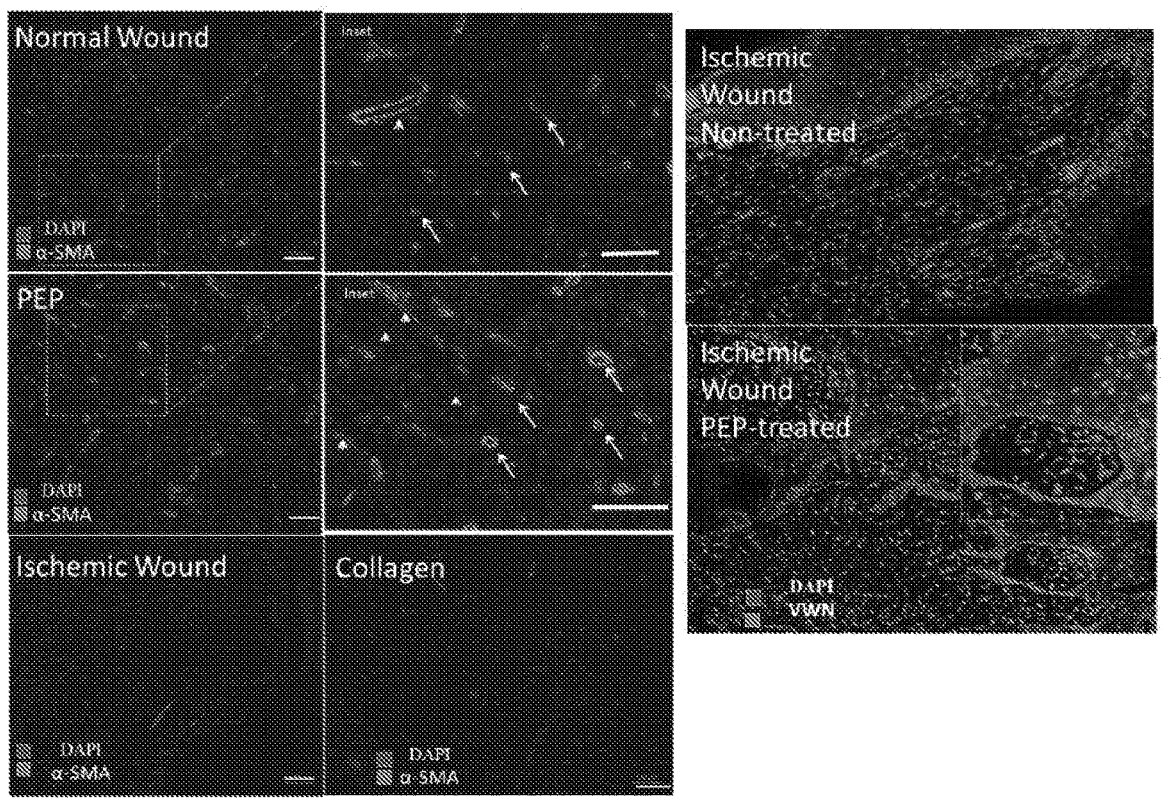
FIG. 8. α-SMA immunohistochemistry staining of cells in wound bed at day 28 postoperative. Differentiated fibroblasts to myofibroblasts pointed with arrows. The α-SMA positive cells around newly formed blood vessels are pointed with arrow heads. *=p-value<0.01.

FIG. 8 shows expression level of ∝-SMA in wound sites treated by PEP for 28 days. The indicated spindled shape ∝-SMA-positive cells in the PEP-treated wound bed are demonstrating the differentiated fibroblasts to myofibroblasts (FIG. 8). In addition, the expression of ∝-SMA in smooth muscle cells around newly formed blood cells (FIG. 8, arrow heads) indicates the initiation of blood vessel formation at these wound beds. A quantitative analysis of ∝-SMA positive cells confirmed that there was a statistically significant difference (p<0.01) between the PEP-treated group and the collagen-treated and untreated groups, corresponding with fibroblast differentiation and a higher density of mature blood vessels.

Induction of New Tissue from Satellite Cells

Figure 9:
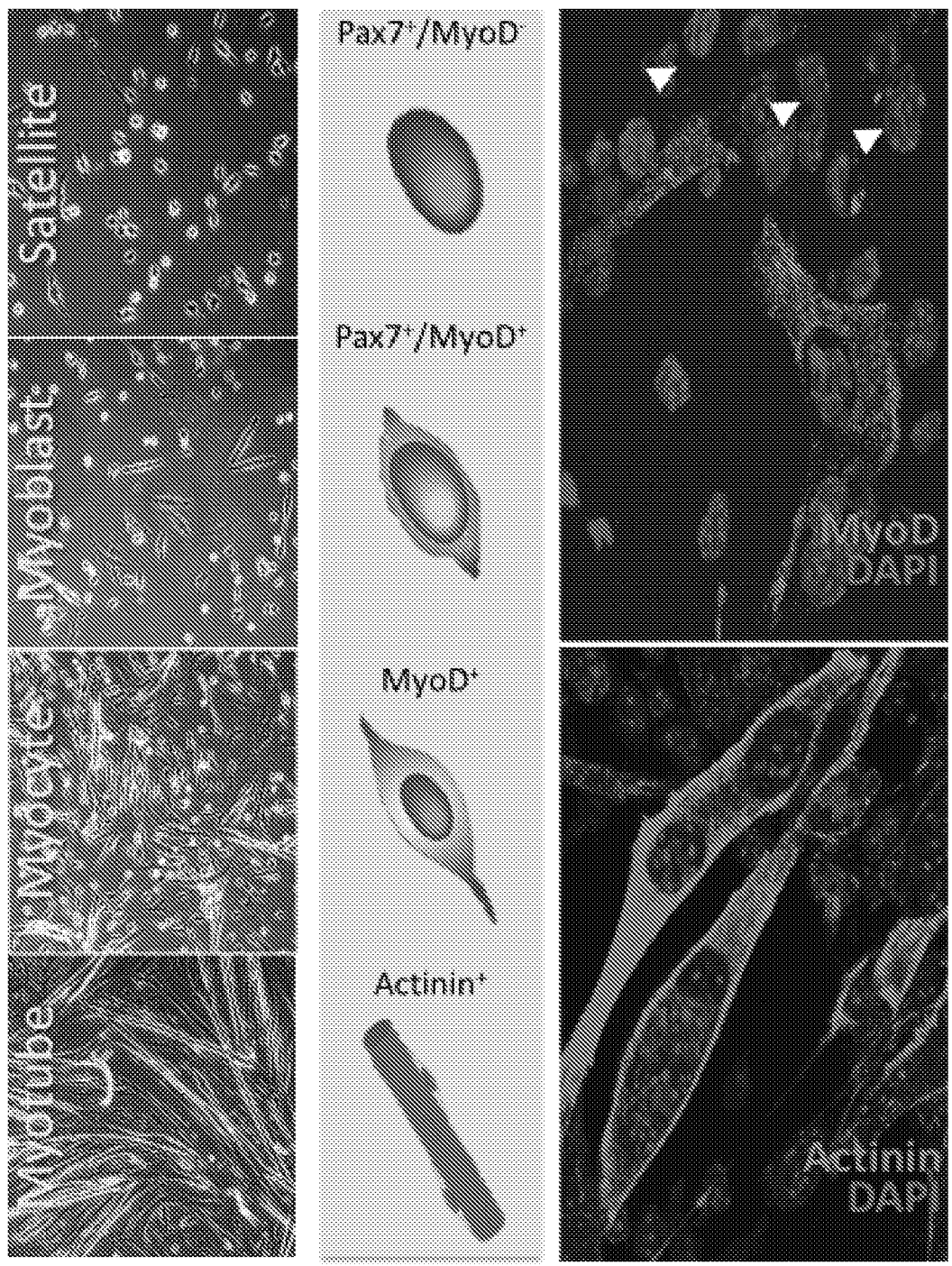
FIG. 9. PEP-guided skeletal muscle growth. PEP induces rapid proliferation of myoblast progenitors (MyoD+ Sateline/myoblast). Altering culture conditions using PEP induced myotube formation in culture (Actinin).
Figure 10:
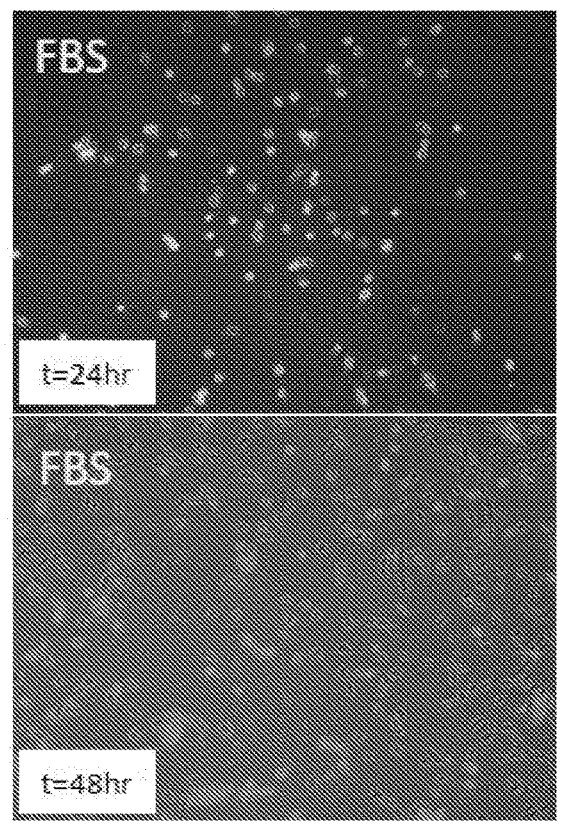
FIG. 10. PEP-guided skeletal muscle growth. PEP induces rapid proliferation of myoblast progenitors after 24 hours and 48 hours (right panels) versus standard culture conditions (FBS). Altering culture conditions using PEP induced myotube formation in culture (PEP 48 h).
Figure 10:
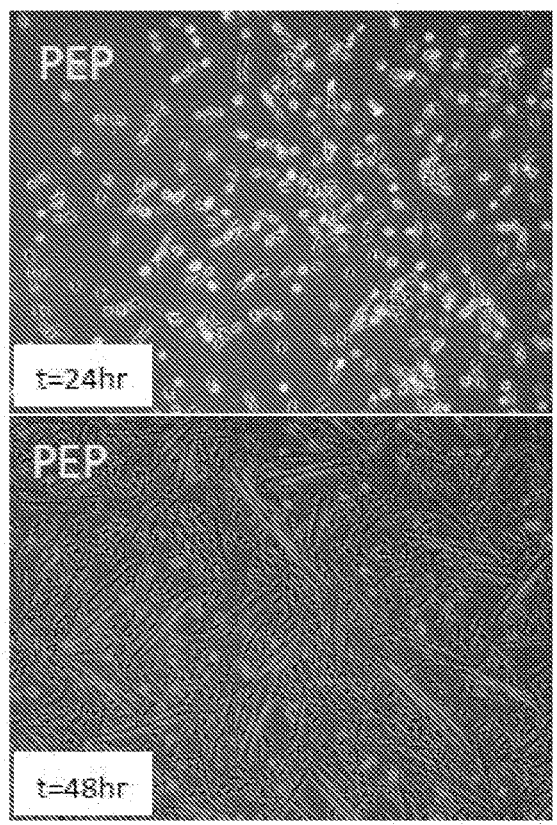
Figure 10:
Figure 10:
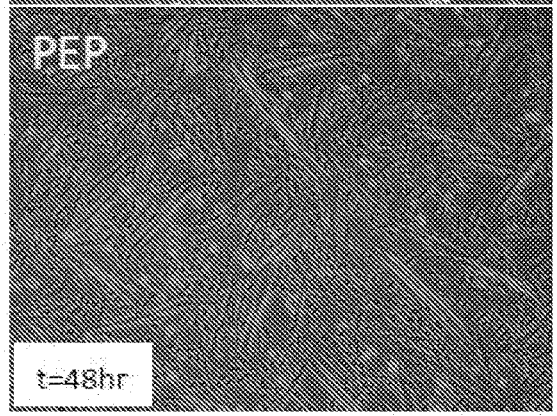
Figure 11:
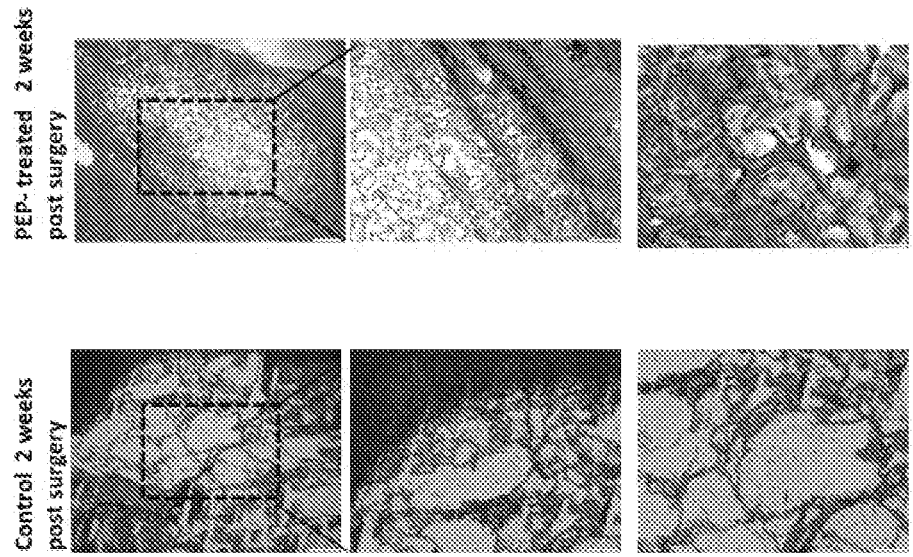
FIG. 11. PEP-guided injury repair. (A) Use of PEP within the subcutaneous space in the setting of muscle injury induced a massive increase in cellularity within a surgical collagen scaffold over a two-week period, not seen in collagen scaffold alone. (B) After a four-week observation period, progenitors had differentiated in either skeletal muscle of adipose tissue in PEP loaded scaffolds (depending on proximity to like tissues) while collagen-only scaffolds remained decellularized.
Figure 11:
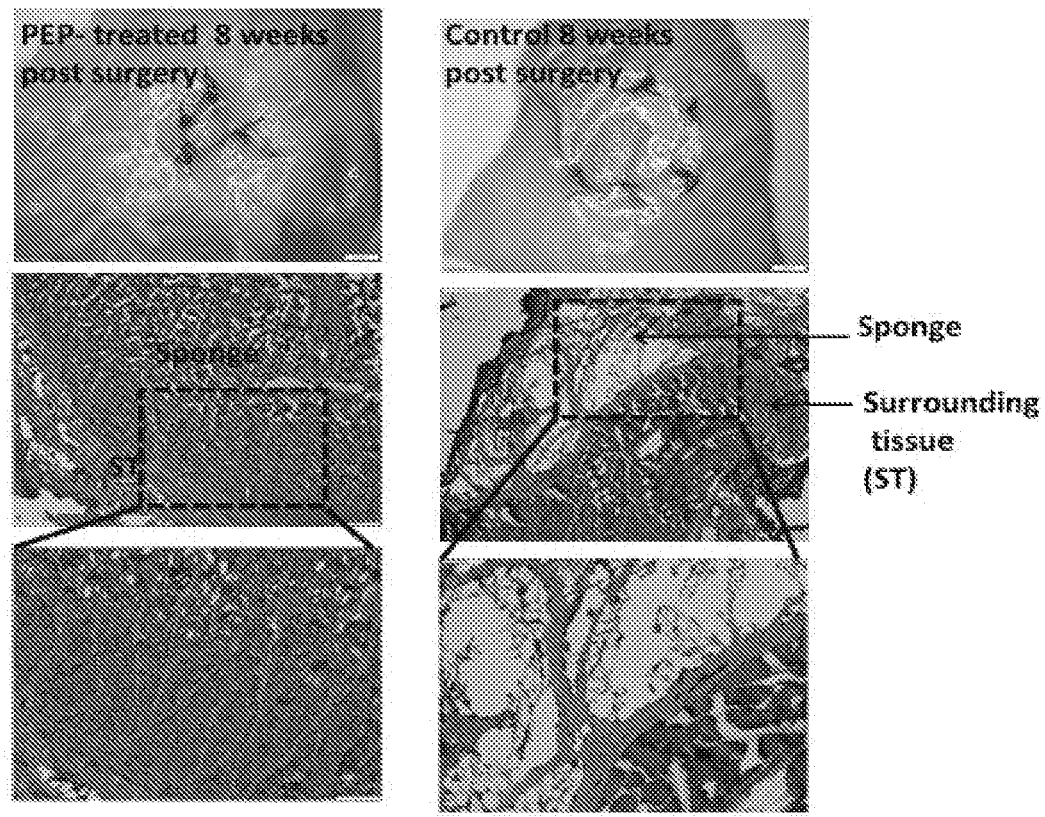

FIG. 9 shows phase, immunofluorescence and graphical depiction of skeletal muscle satellite cells grown in the presence of PEP. Here, a low confluence of satellite cells demonstrated the capacity for proliferation into myoblasts, myocytes (MyoD+) and ultimately organized into functional myotubes (Actinin+). In FIG. 10, these findings are further supported by a head-to head comparison of PEP with other growth conditions such as FBS (or PRP and Platelet lysate not shown) where satellite cells cannot be coaxed to yield functional tissue. In FIG. 11, further demonstration of this paradigm was provided with in vivo testing of collagen matrices either engrafted alone or following PEP enrichment. FIG. 11A and FIG. 11B document that in the PEP enriched conditions, there is robust evidence for skeletal muscle generation as early as two weeks with full thickness restoration of muscle content noted at eight weeks. This regenerative response was not seen in the control (collagen only) group. These data provide the rationale behind the use of a PEP enriched environment to induce regeneration of tissues enriched with progenitors such as the skin, skeletal muscle (including the pharynx/larynx, urinary and anal sphincter, and diaphragm along with those associated with the musculoskeletal system), tissues with smooth muscle including the gastrointestinal tract, vagina, bladder, uterus and other structural organs.

Figure 12:
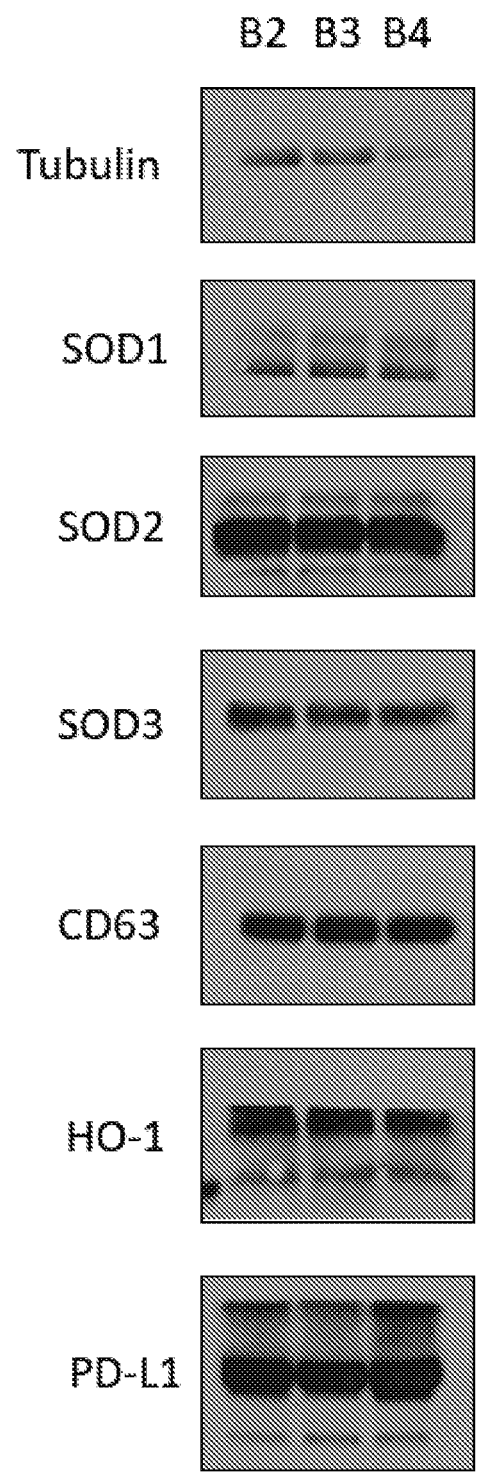
FIG. 12. Western Blot analysis detecting proteins contained in PEP preparations that have activity suppressing oxidative stress. Three different batches of PEP (B2, B3, B4) were dissolved into a 20% solution (5 mL saline in PEP vial), filtered with a 0.2 micron filter and the concentration of proteins was quantified using a BCA assay kit (Pierce, Thermo Fisher Scientific, Inc., Waltham, MA). From this, 1.5 μL of each sample was lysed in 23.5 μL of lysis buffer and heated at 85° C. for three minutes. 20 g of protein were loaded onto a 12.5% polyacrylamide gel (CRITERION, Bio-Rad Laboratories, Inc., Hercules, CA).

FIG. 12 shows Western blot analysis of three different PEP preparations, labelled B2, B3, and B4. Each sample was probed with antibodies that specifically bind to exemplary exosome proteins tubulin, superoxide dismutase 1 (SOD1), superoxide dismutase 2 (SOD2), superoxide dismutase 3 (SOD3), CD63, heme oxygenase (HO-1), and programmed death ligand 1 (PD-L1). Tubulin is a ubiquitous protein in human cells. SOD1, SOD2, and SOD3 are anti-oxidases that limits damage caused by reactive oxygen species (ROS). CD63 is an exosome membrane surface protein. HO-1 is an enzyme that catalyzes the degradation of heme and is induced by oxidative stress. PD-L1 is a transmembrane protein involved in suppressing the immune system during particular events such as pregnancy, tissue allografts, auto-immune disease. FIG. 12 shows that the process used to prepare PEP produces a highly consistent protein profile, as evidenced by the banding of the exemplary proteins across three separately-prepared PEP preparations.

Figure 13:
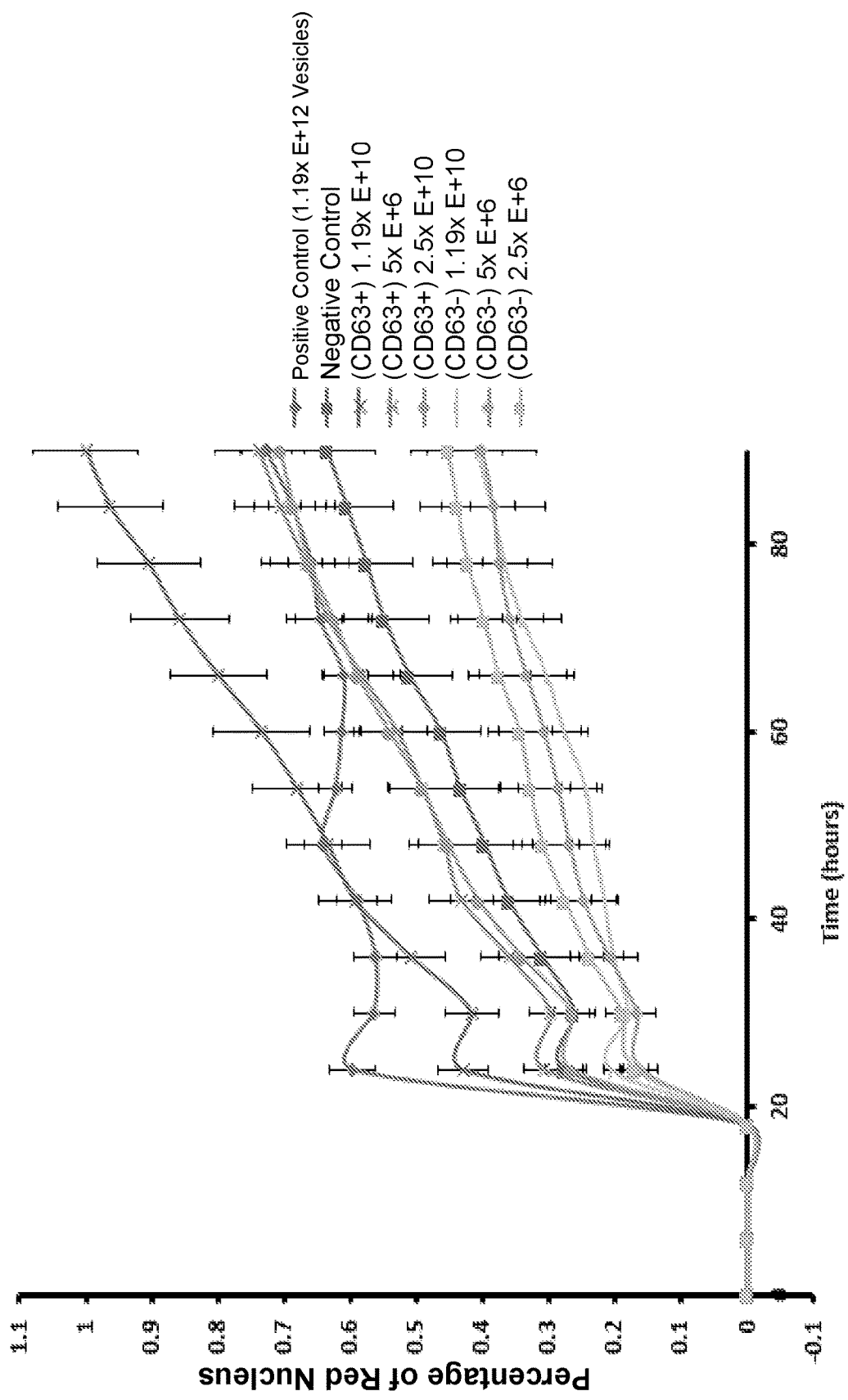
FIG. 13. Analysis of cell growth as a function of time after treatment with the indicated amounts of sorted CD63$^+$ PEP exosomes or the indicated amount of CD63$^-$ PEP exosomes. CD63$^+$ PEP exosomes continuously promoted cell growth compared to the negative control (serum free medium) for the time tested. CD63$^+$ PEP exosomes further promoted continuous growth after about 30 hours, whereas the positive control showed rapid growth for 20 hours, then flat or slow growth thereafter. CD63$^-$ PEP exosomes inhibited cell growth compared to the negative control. The presence of both of these populations in PEP allows for appropriate induction of cell growth for healing, but prevents uncontrolled growth.

FIG. 13 shows time-dependent cell growth using various concentrations of PEP preparations. FIG. 13 also shows the effects of sorting the PEP preparation based on the CD63 expression on the surface of the exosomes in the preparation. A PEP preparation typically includes a mixture of $CD63^+$ exosomes and $CD63^-$ exosomes. $CD63^+$ exosomes may be sorted from the PEP preparation by any method suitable for sorting membrane-bound vesicles. Exemplary methods for sorting $CD63^+$ exosomes include, but are not limited to, affinity separation, magnetic bead separation, flow separation, and the like. The positive control shows cell growth when treated with sham vesicles. Cell growth increases rapidly until hour 20 and then flattens out as the cells reach confluence. In contrast, cells treated with PEP preparations continue to grow (e.g., from hour 20 through hour 60). Cells treated with PEP with $CD63^+$ exosomes show growth that continues at a more-or-less constant rate after about 40 hours. Cells treated with PEP containing $CD63^-$ exosomes also show a more-or-less constant growth rate after about 40 hours, but at a rate less than the negative control (cells grown in serum free medium). Thus, PEP that contains $CD63^+$ exosomes can promote cell growth, as may be desired for applications that involve wound healing and/or tissue regeneration. Unrestrained cell growth, however, can result in the growth of neoplasia. PEP that includes $CD63^-$ exosomes can engage the cells' machinery that slows growth—e.g., upon reaching confluence—and thereby limit the risk that PEP preparations that include $CD63^+$ exosomes result in unrestrained cell growth.

An unmodified PEP preparation—i.e., a PEP preparation whose character is unchanged by sorting or segregating populations of exosomes in the preparation—naturally includes a mixture of $CD63^+$ and $CD63^-$ exosomes. Because $CD63^-$ exosomes can inhibit unrestrained cell growth, an unmodified PEP preparation that naturally includes $CD63^+$ and $CD63^-$ exosomes can both stimulate cell growth for wound repair and/or tissue regeneration and limit unrestrained cell growth. Also, because $CD63^-$ exosomes can inhibit unrestrained cell growth, PEP preparation that is enriched for $CD63^-$ exosomes—e.g., by sorting and removing at least a portion of the $CD63^+$ exosomes—can be used as an anti-neoplastic therapy.

Further, by sorting $CD63^+$ exosomes, one can control the ratio of $CD63^+$ exosomes to $CD63^-$ exosomes in a PEP product by removing $CD63^+$ exosomes from the naturally-isolated PEP preparation, then adding back a desired amount of $CD63^+$ exosomes. In some embodiments, a PEP preparation can have only $CD63^-$ exosomes.

In other embodiments, a PEP Preparation can have both $CD63^+$ exosomes and $CD63^-$ exosomes. The ratio of $CD63^+$ exosomes to $CD63^-$ exosomes can vary depending, at least in part, on the quantity of cell growth desired in a particular application. For example, a $CD63^+/CD63^-$ exosome ratio provides desired cell growth induced by the CD63+ exosomes and inhibition of cell growth provided by the CD63− exosomes achieved via cell-contact inhibition. In certain scenarios, such as in tissues where non-adherent cells exist (e.g., blood derived components), this ratio may be adjusted to provide an appropriate balance of cell growth or cell inhibition for the tissue being treated. Since cell-to-cell contact is not a cue in, for example, tissue with non-adherent cells, one may reduce the CD63+ exosome ratio in order to avoid uncontrolled cell growth. Conversely, if there is a desire to expand out a clonal population of cells, such as in allogeneic cell-based therapy or immunotherapy, one can increase the ratio of CD63+ exosomes in order to ensure that a large population of cells can be derived from a very small source.

Thus, in various embodiments, the ratio of CD63+ exosomes to CD63− exosomes in a PEP preparation may be 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, or 30:1. In certain embodiments, the PEP product is formulated to contain a 9:1 ratio of CD63+ exosomes to CD63− exosomes.

FIG. 14 highlights the size distribution and total exosome yield for techniques such as ultracentrifugation and tangential flow filtration (TFF) versus the method described herein yielding PEP. NanoSight analysis of these discrete techniques shows that the exosome (extracellular vesicle) yield using either ultracentrifugation or TFF results in a broad distribution of exosome sizes ranging from 41 nm to 776 nm in ultracentrifugation and 56 nm to 829 nm in TFF. Conversely, a typical PEP derivation generates a narrower exosome (or extracellular vesicle) size distribution of 65 nm to 280 nm with the bulk of the exosomes residing between 100 nm and 200 nm. Furthermore, the yield of particles per ml for both ultracentrifugation and TFF was $2\times10^8$ whereas the PEP preparation reproducibly yields $6\times10^{11}$ particles/ml.

Figure 15:
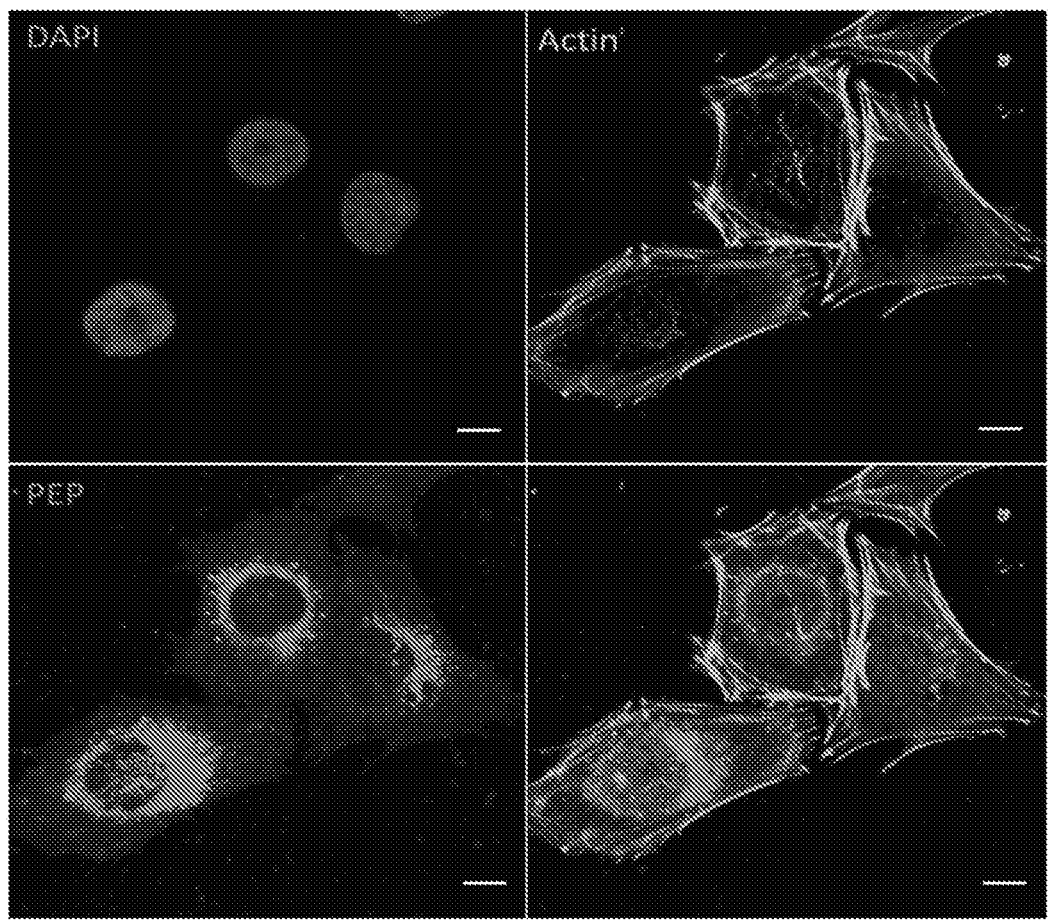
FIG. 15. PEP entry into cells. Immunofluorescence with red fluorescent tagged PEP exosomes demonstrate rapid uptake of this exosome product into cells.
Figure 16:
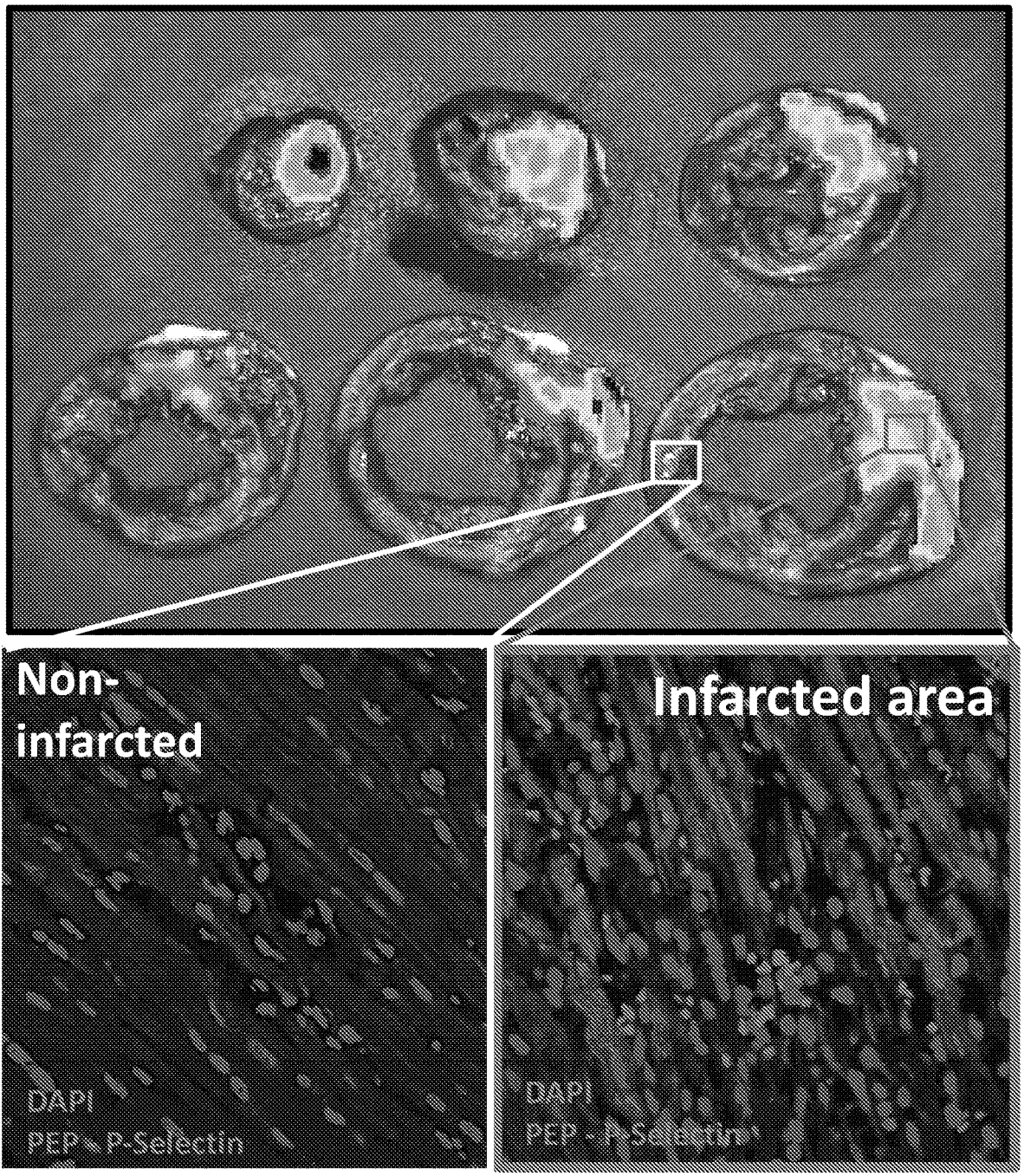
FIG. 16. Delivery of fluorescent labeled PEP into areas of ischemia reperfusion reveals rapid uptake due to capillary leak. PEP labeled with a far-red fluorescent dye was delivered into porcine hearts 10 minutes after relief of a 90-minute occlusion of the left anterior descending artery. Gross analysis of porcine hearts via the Xenogen system reveals presence of the far-red fluorescence in the infarcted territory. Histological analysis shows the presence of p-selectin (an exosome marker) in the infarct territory vs no p-selectin in non-infarct areas. This demonstrates that PEP has the capability to leverage post injury capillary leak to embed into tissues such as the myocardium.

FIG. 15 demonstrates that PEP, when stained with a fluorescent dye, has the capacity to rapidly enter cultured cells. FIG. 16 shows that PEP can also rapidly enter cells when delivered into a tissue environment. Here, PEP is delivered via intracoronary approach in a porcine model of ischemia reperfusion. In this myocardial infarction model, the LAD is occluded using an appropriately sized angioplasty balloon for 90 minutes. Following reperfusion, PEP, labeled with a far-red fluorescent lipid dye, is injected into the left anterior descending. The hearts are harvested within 30 minutes of PEP delivery and grossly evaluated for the far-red signal. As is seen with the generated Xenogen imaging, all of the PEP delivered is trapped within the infarcted territory of the heart (top panel). Histological analysis documented presence of PEP within the myocardial cells in the infarcted, but not in the non-infarcted tissue as tracked by p-Selectin (an exosome marker). This demonstrates that PEP has the capability to leverage post injury capillary leak to rapidly embed into the cells of tissues such as the myocardium. Furthermore, this provides the rationale for intra-arterial delivery of PEP either in the setting of injury or to prevent organ injury.

Figure 17:
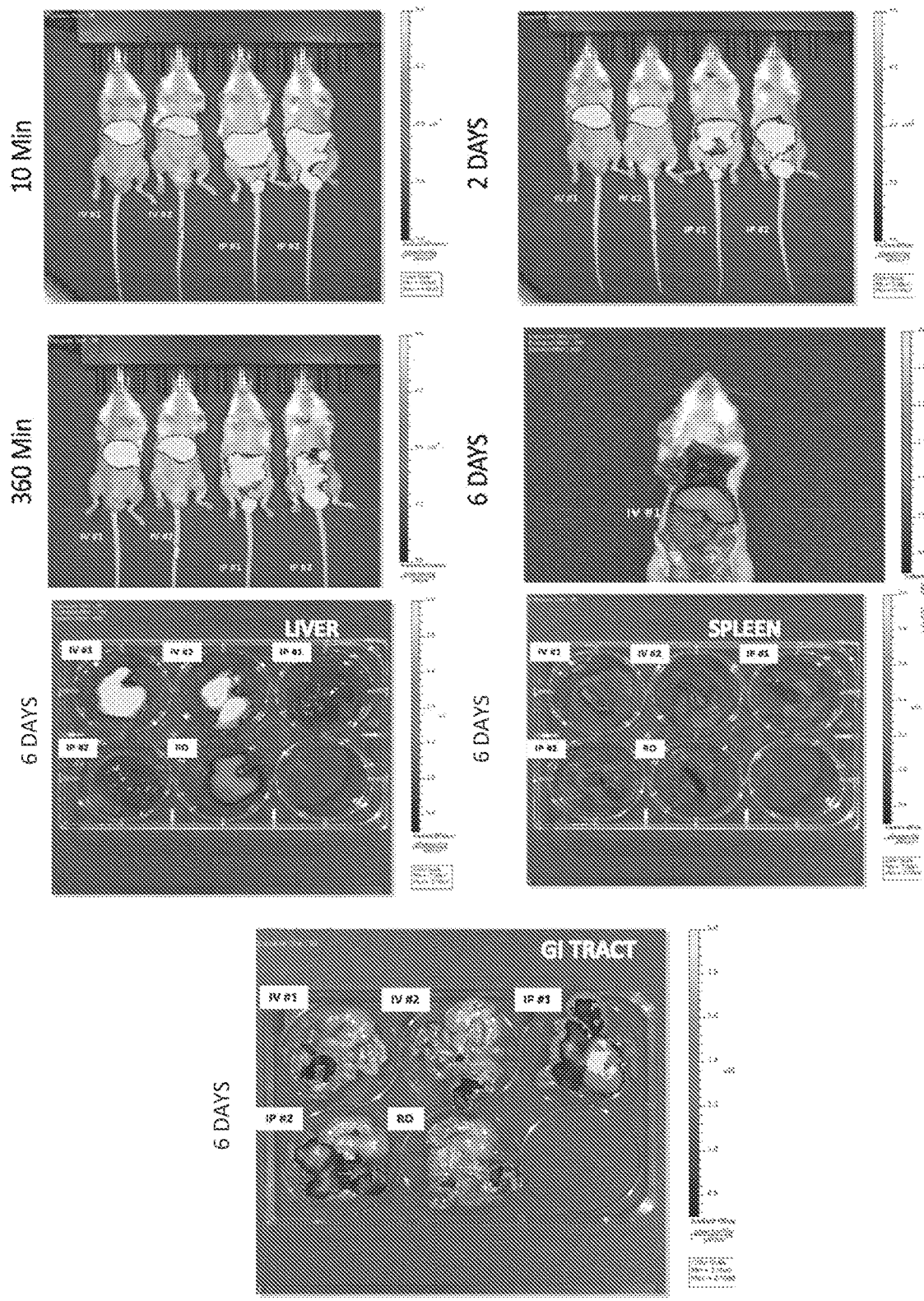
FIG. 17. Biodistribution of PEP labeled with far-red fluorescent dye is noted target the liver when given IV and the GI tract when given IP as visualized by the Xenogen system.

FIG. 17 tracks the biodistribution of PEP when delivered Intravenously (IV) and Intraperitoneally (IP). Over the observation period spanning 10 minutes to six days, nearly all of PEP distributed into the liver when delivered IV with a minority of signal seen in the spleen. IP delivery sequesters PEP to the GI track with no hepatic and minimal splenic involvement. IV delivery via a retro-orbital approach (RO) revealed no significant differences in biodistribution. This suggests that PEP can be delivered IV in health and disease if hepatic targeting is desired.

This disclosure therefore describes a novel exosome-based therapy and exosome-based therapeutic composition. The bio-potency of the exosome-based compositions described is higher than conventional exosome preparations. The small ultrastructural differences between the exosome compositions described herein compared to conventional exosome preparations affect cellular uptake and utilization and, therefore, different structural compositions lead to different effects. Upon inspection under atomic force microscopy (AFM), one can see that our novel purified exosomal product (PEP) does not form clusters or aggregates. This was not the case with platelet rich plasma (PRP) which tends to form snow-flake or floral patterns (FIG. 3). Functionally, PEP, was significantly superior to fetal bovine serum (FBS) or other formulations of conventionally purified exosomes for wound healing, vascularization of the wound bed, and re-epithelialization of the wound. Thus, isolating and purifying exosomal products as described herein—i.e., in a way that ensures a uniform, singular ultrastructural composition as opposed to forming tertiary structures—results in the dramatic upregulation in bio-potency as was shown in vitro and culminates when complexed with collagen in a bio-potentiated matrix. This can induce regeneration of non-healing wound beds back to that which is seen in non-ischemic wounds.

Conventional technologies for promoting wound healing and/or tissue regeneration can be limited by the size of the tissue being treated. Tissue satellites would be placed as poles of regenerative tissue spaced at approximately 3 mm to 5 mm apart. East tissue pole would size approximately 50 μm to 500 μm and can be prepared at the bedside with physical dissection of small amounts of resected healthy tissue adjacent to the area of disease or injury. PEP preparations in combination with a biocompatible support (e.g., a biocompatible web, biocompatible matrix, biocompatible scaffold, etc.) can overcome this limitation for tissue regeneration by providing multiple "satellite" nuclei of tissue growth. Each satellite nucleus can include a biocompatible support to which a PEP preparation is adhered, adsorbed, or otherwise attached. The satellite nucleus (cell or tissue cluster) can further include additional growth factors. When a plurality of satellite nuclei is used, the composition of each satellite nucleus can be independently designed to be the same as, or different than, any other satellite nucleus. In use, the satellite nuclei can be positioned within the damaged tissue according to the location or locations where tissue regeneration is desired. The spacing of the satellite nuclei can be 3 mm to 5 mm apart. The satellite nuclei can serve as the focal point of tissue regeneration occurring in parallel between the various nuclei until tissue regenerating from the various satellite nuclei coalesce to form continuous regenerated tissue. FIG. 9 shows an example of how cell or tissue satellites can yield a confluence of skeletal muscle tissue in the setting of PEP.

In the preceding description and following claims, the term "and/or" means one or all of the listed elements or a combination of any two or more of the listed elements; the terms "comprises," "comprising," and variations thereof are to be construed as open ended—i.e., additional elements or steps are optional and may or may not be present; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Manufacturing the Purified Exosome Product (PEP)

Apheretic blood product were harvested from certified blood banks, confirming adherence to best clinical standards. Products units are frozen to either −20° C. or −80° C. and stored within a Current Good Manufacturing Practices (CGMP) facility.

To initiate the manufacturing process 2-30 units were thawed (typically 5-15), undergo a gravity-based filtration step using a 20 µm-40 µm filter, and were pooled as a combined product with several agitation steps prior to being refrozen to −20° C. to −80° C. The poled product was agitated with five minutes of manual agitation followed by 5-15 minutes of mechanical agitation. Under controlled conditions, the pooled product was thawed at a rate of 0.1° C. to 5° C. and sequestered by specific volumes into sterile glass vials. Depending on the level of moisture content desired, volumes as little as 0.1 ml to 10 mls may be utilized in vials as small as 1 ml and as large as 50 ml. Aliquoted products next undergo modulated temperature changes to ensure a uniform cryodesiccation profile. The desiccation process can take as little as five hours and as long as 170 hours. The final product after this procedure is visually released based on caked pellet formation, with release criteria requiring more than 95% appropriate caking per lot manufactured. If these metrics are not met, the entire lot is decommissioned.

Manufacturing the Collagen-PEP Scaffold

Purified Exosome Product (PEP) was obtained by lyophilizing the frozen exosome-rich solution for 48 hours. 3 mg/ml concentration collagen was mixed with the lyophilized PEP to achieve the final concentration of 20% w/v. The mixed solution was poured gently into a 6-cm petri dish and incubated at 37° C. FIG. 1A demonstrates the various steps in the manufacturing process of PEP. FIG. 1B is a schematic diagram that illustrates the relationship between PEP and collagen fibers.

Scanning Electron Microscopy (SEM)

Using a Field Emission—Scanning Electron Microscope (Hitachi S-4700, Hitachi High-Technologies, Tokyo, Japan) The morphological characteristics of collagen (FIG. 2A, 2B) and collagen-PEP (FIG. 2C, 2D) scaffolds were observed. Scaffolds were fixed in 2.5% glutaraldehyde in 0.1 M sodium phosphate buffer, pH 7.2, overnight. Samples were subsequently post-fixed in 1% osmium tetroxide for one hour, dehydrated in ethanol, and critical point dried. Dried samples were coated with gold via a sputter-coater at ambient temperature. Micrographs of scaffolds were taken and the pore size distribution was determined using Beckman Coulter LS 32 equipment with a range of 0.01 mm to 1,000 mm. The average pore size was calculated by measuring the pore size of 30 pores on each of the six SEM photos.

Atomic Force Microscopy (AFM)

Atomic force microscopy was employed to investigate the morphology of collagen and bio-potentiated PEP. Collagen or PEP was placed on the surface of freshly cleaved mica discs and incubated for approximately 30 minutes at 37° C. After incubation, samples were washed with water 4-5 times and then dried with nitrogen gas. Nanoscale AFM images (512×512 pixels) were collected in tapping mode using a Nanoscope IV PicoFroce Multimode AFM (Bruker Corporation, Billerica, MA) at room temperature and analyzed using Nanoscope Analysis Version 1.40 software (Park, S. & Terzic, A, 2010. *J Struct Biol* 169:243-251). Representative images are shown in FIG. 3.

Human Dermal Fibroblasts (HDF) Migration Assay:

HDFs were seeded in 96-well INCUCYTE IMAGELOCK tissue culture plate (Essen BioScience, Inc., Ann Arbor, MI) plates at $2 \times 10^4$ cells per well and were cultured in a humidified 37° C., 5% $CO_2$ incubator. 24 hours later, the INCUCYTE WOUNDMAKER was used to create precise and reproducible wounds in all wells of the 96-well IMAGELOCK plate. After wounding; the media was aspirated from each well and the wells were gently washed two times with culture media to prevent dislodged cells from settling down and reattaching. After a wash with PBS buffer, 100 µL of culture medium was replaced by PEP in solution diluted with DMEM (without FBS) at 5% w/v concentration to determine the effect of PEP on HDF migration. The cells that were subsequently cultured with DMEM (with FBS) were regarded as controls. After being cultured, assay plate was placed into the INCUCYTE ZOOM and the system was allowed to equilibrate for five minutes. Repeat scanning (every three hours for 48 hours) in the ZOOM software was scheduled and images were taken and recorded. The first scan in the time course was used to generate the initial scratch wound mask (a digital overlay showing the border/leading edge of the migrating cells and the non-wounded area). This initial scratch wound mask was used in subsequent quantification processes. Scratch wound masks were also computed for all subsequent image time points after the first scan. In addition, statistical analysis of HDF migration assay was performed; we measured the Relative Wound Density (RWD) that relies on the initial scratch wound mask to differentiate between cell-occupied and cell-free regions of the image. Results are shown in FIG. 4.

Angiogenesis Assay (In Vitro Tube Formation)

To perform the in vitro angiogenesis and tube formation, PrimeKit-Cryo (Essen BioScience, Inc., Ann Arbor, MI) was used. On Day 0, the NHDF (Normal Human Fibroblast) are thawed, rinsed, and plated in seeding media into a Corning 96-well plate. The NHDFs are then incubated at room temperature in a tissue culture hood for one hour to allow them to adhere to the plate. Following seeding of the HUVEC CytoLight Green, the plate is incubated at room temperature for one hour prior to placing in the INCUCYTE for imaging. The cell densities for the PrimeKit have been optimized to conform to our strict quality control guidelines for assay performance. Following seeding, co-cultures are placed in an INCUCYTE S3 and images are automatically acquired in both phase and fluorescence every three hours for eight days using the Tiled Field of View (FOV) mosaic imaging mode. In this mode, six total images (3 images wide×2 images high) are acquired per well and merged into a single, larger image covering nearly 50% of the well (FIG. 5A). On Day 1 the seeding media was replaced with 150 µL growth media (provided with the kit) per well. On Day 2 test reagents (5% PEP or 5% PRP or 10% FBS) were added in assay media. On Day 4 and Day 7, test reagents were replaced with fresh test reagents media. The progress was monitored for eight days; tube formation was processed dynamically using integrated INCUCYTE algorithms.

Animal Model and Rabbit Surgery

Under general anesthesia and using aseptic technique, the rabbit ears were prepped and hair was trimmed using surgical clippers. Subsequently, an ischemic wound was created as previously described (Ahn, S. T. & Mustoe, T. A, 1990. *Ann Plast Surg* 24:17-23). Briefly, with selective division of one or more of the three arteries and veins an ischemic substrate was generated with wounds at the base of rabbit years closed with interrupted 3-0 Nylon sutures. To create an ischemic wound, a circular, full-thickness lesion was created on the ventral ear with a 2-cm punch. The bioscaffold was applied in the experiment group to the wound before applying sterile dressing while in the control groups, the wounds were only covered with sterile dressing.

Histology

To assess cellular infiltration into the wounded site of the skin, samples from three wounds per group were collected at the desired time point. To obtain skin sample from the biopsied area, rabbits were scarified and tissue were removed by dissection. Wounded areas of skin tissue were subsequently placed on a filter membrane for stabilization (any membrane that is resistant to organic solvents such as nitrocellulose) and the samples were cut exactly into half. Half wounds were embedded either directly in Optimal Cutting Temperature (OCT) tissue freezing medium (for cryo-sections) or were fixed overnight with 4% paraformaldehyde and embedded in paraffin so that the sectioning can start in the middle of the wound. Formalin-fixed samples were sectioned at 8 μm and stained with hematoxylin and eosin.

Hemotoxylin and Eosin (H&E) Staining

8-μm paraffin section of skin tissue, processed, sectioned, and de-waxed and rehydrated by serial incubation in xylene (2×3 minutes), 50:50 xylene/100% ethanol (1×3 minutes), 100% ethanol (2×3 minutes), 95% ethanol (1×3 minutes), 70% ethanol (1×3 minutes), 50% ethanol (1×3 minutes), and finally in $H_2O$ (1×5 minutes). Slides were stained with Harris hematoxylin solution (HHS32, Sigma-Aldrich, St. Louis, MO) for five minutes at room temperature and subsequently were rinsed under running tap water in staining jar until the water was no longer colored (approximately five minutes). Slides were dunked into Acid Alcohol (1% HCl in 70% EtOH) two or three times until the sections turn pink. Slides were rinsed with tap water for three to five minutes, and then were dunked in ammonia water (1 mL $NH_4OH$ in 1 L $H_2O$) for five or six times until sections were darkened noticeably. Slides were rinsed with tap water for three to five minutes, followed be adding eosin Y aqueous solution (HT110232, Sigma-Aldrich, St. Louis, MO) to slides for one minute. Slides were again rinsed under running tap water for three to five minutes. Slides then were dehydrated by serial incubation in 95% ethanol (2×3 minutes), 100% ethanol (2×3 minutes), 50:50 xylene/100% ethanol (1×3 minutes) and xylene (2×3 minutes). Slides were kept in xylene (no longer than one hour) until they were cover slipped using Permount or a xylene-based mounting medium.

Immunohistochemistry

8-μm paraffin section of skin tissue, processed, sectioned, de-waxed, and rehydrated by serial incubation in xylene (2×3 minutes), xylene:ethanol (1×3 minutes), 100% ethanol (2×3 minutes), 95% ethanol (1×3 minutes), 70% ethanol (1×3 minutes), 50% ethanol (1×3 minutes) and finally in $H_2O$ (1×5 minutes). Thereafter, antigen retrieval was performed by immersing the tissue sections in Tris-EDTA buffer (10 mM Tris, 1 mM EDTA pH 8) or in 0.01 M citrate buffer (pH 6) that had been pre-heated for three minutes in a microwave (850 W). The slides were heated for 10 minutes at 360 W. Following this, the slides were allowed to cool to room temperature (RT) for 30 minutes before washing in 1×PBS. Sectioned were incubated with 0.1% Triton in PBS for five minutes and then washed in PBS three times for five minutes per wash. Sections were taken through to the blocking step immediately. Non-specific binding of the primary antibody was blocked by incubating sections with 10% goat serum, 1% BSA, 0.01% triton, diluted in PBS for one hour at room temperature prior to antibody incubation. After one hour of blocking, slides were gently tapped onto blotting paper to remove the blocking solution. Primary antibodies were diluted in 0.5% BSA in PBS and each section was incubated with 120 μl primary antibodies at 4° C. overnight in humidity chamber. Negative controls were incubated in 0.5% BSA/PBS, omitting the primary antibody. Post incubation, unbound primary antibody was removed by washing in PBS three times for three minutes per wash. Thereafter, each slide was incubated with 120 μl poly-HRP-anti-mouse/rabbit/rat IgG for one hour at room temperature.

After washing in PBS (3×5 minutes), coverslips were mounted using Mowie Oil and left to harden at room temperature. Results were visualized and photographed on a Confocal Leica microscope.

Confocal Microscopy

All images were acquired on a Leica TCS-SP5 confocal microscope at 40× or 20× magnification. Excitation lasers for fluorescein isothiocyanate (FITC) and tetramethyl rhodamine isothiocyanate (TRITC) dyes were standardized for each experiment, with DAPI dye set by eye for each image as required. Image processing was carried out using PHOTOSHOP 7.0 imaging software (Adobe Systems Inc, San Jose, CA).

Example 2

Three different batches of PEP (B2, B3, B4) were dissolved into a 20% solution (5 mL saline in PEP vial), filtered with a 0.2 micron filter and the concentration of proteins was quantified using a BCA assay kit (Pierce, Thermo Fisher Scientific, Inc., Waltham, MA). From this, 1.5 μL of each sample was lysed in 23.5 μL of lysis buffer, and heated at 85° C. for three minutes. 20 g of protein were loaded onto a 12.5% polyacrylamide gel (CRITERION, Bio-Rad Laboratories, Inc., Hercules, CA).

Results are shown in FIG. 12.

Example 3

Milteni CD63 magnetic beads were utilized to separate positive and negative exosome populations. These populations were pelleted down and quantified prior to serial dilutions for culture-based assessment. In an IncuSite system cultured HUVEC were placed in 5% PEP (positive control), serum free solution (negative control), and the described CD 63+/CD63-concentrations. Results are shown in FIG. 13.

Example 4

Exosome populations were purified using Ultracentrufugation at 30,000×g for 16 hours, Tangential Flow Filtration using a 50 KDa weight delimitation filter versus the PEP derivation process. Ultracentrifugation and TFF-derived samples in liquid form are diluted 1000× and put into the NanoSight for analysis. Lyophilized PEP is dissolved into sterile water as a 100% solution and diluted 1000× prior to assessment in the NanoSight system (the gold standard for EV characterization) for size distribution and quantification. Results are shown in FIG. 14.

Example 5

Fluorescent lipid dye in the RFP and Far-Red range were added to a 20% PEP preparation and Centrifuged at 17,000×g for 10 minutes to wash off the unbound dye. The resuspended pellet is sonicated for homogenization and filtered via 0.2 μm filter to remove debris prior to delivery into a cell culture condition (FIG. 15), intracoronary delivery following myocardial infarction (FIG. 16) and IV delivery for biodistribution analysis (FIG. 17).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method of preparing a purified exosome product, the method comprising:
   obtaining material comprising:
      blood,
      a blood product, or
      a non-blood product comprising:
         umbilical cord Wharton's jelly,
         stromal vascular fraction of fat,
         apheresis bone marrow products,
         synovial fluid,
         cerebrospinal fluid, or
         mesenchymal stem cells;
   filtering or apheresing the material;
   pooling the material;
   agitating the material under conditions effective to maintain spherical or spheroid structure of exosomes in the material;
   freezing the agitated material under conditions effective to maintain spherical or spheroid structure of exosomes in the material;
   thawing the frozen agitated material at a controlled rate of from 0.1° C. to 5° C. per minute; and
   cryodesiccating the agitated material comprising freezing the agitated material at a controlled rate.

2. The method of claim 1, wherein the material is obtained from a person under the age of 30, a post-surgical donor, a pre-menopausal woman, a peripartum woman, or a placenta.

3. A method of preparing an artificial blood product, the method comprising:
   preparing a purified exosome product according to the method of claim 1; and
   reconstituting the purified exosome product in a pharmaceutically acceptable carrier.

4. The method of claim 3, further comprising mixing the artificial blood product with a biodegradable polymer scaffold, a non-biodegradable polymer scaffold, or a nanotube.

5. The method of claim 1, wherein the material comprises umbilical cord blood.

6. The method of claim 1, further comprising freezing the material at a temperature no warmer than −20° C.

7. The method of claim 1, wherein filtering the material comprises using gravity-based filtration.

8. The method of claim 1, further comprising sequestering the material prior to being cryodesiccated.

9. The method of claim 1, wherein the agitated material is cryodesiccated for at least five hours.

10. The method of claim 9, wherein the agitated material is cryodesiccated for up to 170 hours.

11. The method of claim 1, wherein the material comprises blood from a pre-menopausal woman.

12. The method of claim 1, wherein the material comprises blood from a peripartum woman.

13. The method of claim 1, wherein the material comprises blood from a placenta.

14. The method of claim 1, wherein the material comprises blood from an umbilical cord.

15. The method of claim 1, wherein the material comprises jelly from an umbilical cord.

16. The method of claim 1, wherein cryodesiccating the agitated material comprises cooling the agitated material at a rate of from 0.1° C. per minute to 2° C. per minute.

17. The method of claim 1 wherein at least a portion of the spherical or spheroid exosomes have a diameter of no more than 300 nm.

18. A method of preparing a purified exosome product, the method comprising:
   obtaining material comprising:
      blood,
      a blood product, or
      a non-blood product comprising:
         umbilical cord Wharton's jelly,
         stromal vascular fraction of fat, apheresis bone marrow products,
synovial fluid,
cerebrospinal fluid, or
mesenchymal stem cells;
filtering or apheresing the material;
pooling the material;
agitating the material under conditions effective to maintain spherical or spheroid structure of exosomes in the material;
freezing the agitated material under conditions that maintain spherical or spheroid structure of exosomes in the material;
thawing the frozen agitated material at a controlled rate of from 0.1° C. to 5° C. per minute; and
cryodesiccating the agitated material under conditions that maintain spherical or spheroid structure of exosomes in the material.

19. The method of claim 18 wherein at least a portion of the spherical or spheroid exosomes have a diameter of no more than 300 nm.

20. The method of claim 18, wherein the material is obtained from a person under the age of 30, a post-surgical donor, a pre-menopausal woman, a peripartum woman, or a placenta.

21. The method of claim 18, wherein the material comprises umbilical cord blood.

22. The method of claim 18, further comprising freezing the material at a temperature no warmer than −20° C.

23. The method of claim 18, wherein filtering the material comprises using gravity-based filtration.

24. The method of claim 18, further comprising sequestering the material prior to being cryodesiccated.

25. The method of claim 18, wherein the agitated material is cryodesiccated for at least five hours.

26. The method of claim 25, wherein the agitated material is cryodesiccated for up to 170 hours.

27. The method of claim 18, wherein the material comprises blood from a pre-menopausal woman.

28. The method of claim 18, wherein the material comprises blood from a peripartum woman.

29. The method of claim 18, wherein the material comprises blood from a placenta.

30. The method of claim 18, wherein the material comprises blood from an umbilical cord.

31. The method of claim 18, wherein the material comprises jelly from an umbilical cord.

32. A method of preparing an artificial blood product, the method comprising:
preparing a purified exosome product according to the method of claim 18; and
reconstituting the purified exosome product in a pharmaceutically acceptable carrier.

33. The method of claim 32, further comprising mixing the artificial blood product with a biodegradable polymer scaffold, a non-biodegradable polymer scaffold, or a nanotube.

34. The method of claim 18, wherein cryodesiccating conditions comprise cooling the agitated material at a rate of from 0.1° C. per minute to 2° C. per minute.

35. A composition comprising cryodesiccated spherical or spheroid exosomes, wherein at least a portion of the cryodesiccated spherical or spheroid exosomes have a diameter of no more than 300 nm, wherein the spherical or spheroid exosomes are made according to the method of claim 1.

36. An artificial blood product comprising the composition of claim 35 reconstituted in a pharmaceutically acceptable buffer.

37. An artificial blood product comprising: cryodesiccated spherical or spheroid exosomes reconstituted in a pharmaceutical buffer, wherein at least a portion of the cryodesiccated spherical or spheroid exosomes have, while desiccated and prior to reconstitution, a diameter of no more than 300 nm, wherein the spherical or spheroid exosomes are made according to the method of claim 1.

38. A method for accelerating wound healing, the method comprising:
administering the artificial blood product of claim 36 to a wound in an amount effective heal the wound in less time than the wound would heal without being treated.

39. A method for increasing vascularization of a wound bed, the method comprising:
administering the artificial blood product of claim 36 to a wound in an amount effective heal the wound in less time than the wound would heal without being treated.

40. A method for increasing epithelization of a wound, the method comprising:
administering the artificial blood product of claim 36 to a wound in an amount effective heal the wound in less time than the wound would heal without being treated.

41. A method for inhibiting neoplasia in a tissue, the method comprising:
administering the artificial blood product of claim 36 to a tissue exhibiting neoplasia.

* * * * *